United States Patent
Masutani et al.

(10) Patent No.: US 9,347,037 B2
(45) Date of Patent: May 24, 2016

(54) METHODS AND APPARATUS FOR BUILDING COMPLEX 3D SCAFFOLDS AND BIOMIMETIC SCAFFOLDS BUILT THEREFROM

(71) Applicants: Evan Masataka Masutani, Honolulu, HI (US); Brandon Aran Yoza, Honolulu, HI (US); Travis Tadashi Tanaka, Kailua, HI (US); Christopher Randall Russ, Hampton, VA (US); Andrew Kevin Donald Ellison, Honolulu, HI (US); Dominic Seth Reiss, Honolulu, HI (US)

(72) Inventors: Evan Masataka Masutani, Honolulu, HI (US); Brandon Aran Yoza, Honolulu, HI (US); Travis Tadashi Tanaka, Kailua, HI (US); Christopher Randall Russ, Hampton, VA (US); Andrew Kevin Donald Ellison, Honolulu, HI (US); Dominic Seth Reiss, Honolulu, HI (US)

( * ) Notice: Subject to any disclaimer, the term of this patent is extended or adjusted under 35 U.S.C. 154(b) by 0 days.

(21) Appl. No.: 14/176,939

(22) Filed: Feb. 10, 2014

(65) Prior Publication Data

US 2014/0227783 A1 Aug. 14, 2014

Related U.S. Application Data

(60) Provisional application No. 61/780,802, filed on Mar. 13, 2013, provisional application No. 61/763,450, filed on Feb. 11, 2013.

(51) Int. Cl.
C12N 5/00 (2006.01)

(52) U.S. Cl.
CPC ............ *C12N 5/0062* (2013.01); *C12N 5/0068* (2013.01); *C12N 2533/54* (2013.01); *C12N 2533/70* (2013.01); *C12N 2537/10* (2013.01)

(58) Field of Classification Search
None
See application file for complete search history.

(56) References Cited

U.S. PATENT DOCUMENTS

| | | | | |
|---|---|---|---|---|
| 5,202,311 | A * | 4/1993 | Folkman | A61K 9/0019 514/13.2 |
| 5,834,232 | A * | 11/1998 | Bishop et al. | 435/68.1 |
| 6,831,058 | B1 * | 12/2004 | Ikada | A61K 9/1658 514/16.7 |
| 7,192,693 | B2 | 3/2007 | Bryant et al. | |
| 7,303,814 | B2 * | 12/2007 | Lamberti | A61L 27/26 428/357 |
| 7,358,089 | B2 | 4/2008 | Suzuki | |
| 2003/0003157 | A1 | 1/2003 | Ohan et al. | |
| 2003/0179354 | A1 * | 9/2003 | Araki et al. | 355/53 |
| 2006/0094318 | A1 * | 5/2006 | Matsuda et al. | 442/123 |
| 2006/0251719 | A1 * | 11/2006 | Tabata | 424/468 |
| 2008/0112998 | A1 | 5/2008 | Wang | |
| 2009/0239302 | A1 | 9/2009 | Decher et al. | |
| 2009/0269404 | A1 * | 10/2009 | Ishiguro et al. | 424/484 |
| 2010/0028407 | A1 * | 2/2010 | Del Priore et al. | 424/443 |
| 2010/0167401 | A1 | 7/2010 | Hasirci et al. | |
| 2011/0275795 | A1 | 11/2011 | Song et al. | |
| 2012/0100185 | A1 | 4/2012 | Wen et al. | |
| 2013/0172985 | A1 | 7/2013 | Prestwich et al. | |

FOREIGN PATENT DOCUMENTS

| | | | |
|---|---|---|---|
| JP | 11047258 | A * | 2/1999 |
| JP | 2006333727 | A * | 12/2006 |
| WO | 2013025766 | A1 | 2/2013 |

OTHER PUBLICATIONS

JP 11047258. Derwent English abstract. Published Feb. 1999.*
JP 11047258. English Machine Translation. Published Feb. 1999.*
JP 2006333727. Derwent English abstract. Published Dec. 2006.*
JP 2006333727. Published Dec. 2006. English Translation.*
Zinin P. V., Misra A., Kamemoto L., Yu Q., Sharma S. K. 2007 Emulated transmission in confocal Raman microscopy J. Opt.Soc. Am. B 24, 2779.
Schmeichel KL, Bissell MJ (2003) Modeling tissue specific signaling and organ function in three dimensions. J. Cell Sci 116(12): 2377-2388.
Cukierman E, Pankov R, Stevens DR, Yamada KM (2001) Taking cell matrix adhesions to the third dimension. Science 294: 1708-1712.
Tsang VL, Bhatia SN (2006) Fabrication of three dimensional tissues. Adv. Biochem. Eng. Biotechnol. 103:189-205.
Ott HC, Clippinger B, Conrad C, Schuetz C, Pomerantseva I, Ikonomou L, Kotton D, Vacanti JP (2010) Regeneration and orthotopic transplantation of a bioartificial lung. Nat. Med. 16(8): 927-33.
Owen SC, Shoichet MS (2010) Design of three-dimensional biomimetic scaffolds. J. Biomed. Mater. Res. A. 94(4): 1321-1331.
Bártolo PJ, Domingos M, Patricio T, Cometa S, Mironov V (2011) Biofabrication strategies for tissue engineering. In: Fernandes PR, Bártolo PJ, editors. Advances on Modeling in Tissue Engineering. Dordrecht: Springer Netherlands. vol. 20, pp. 137-176.

(Continued)

*Primary Examiner* — Renee Claytor
*Assistant Examiner* — Susan E Fernandez
(74) *Attorney, Agent, or Firm* — Seth M Reiss, AAL, ALLLC

(57) ABSTRACT

A novel method for building complex three-dimensional scaffolds for biomimetic applications such as in vitro organ growth, using a gelatin/sugar/water gel, ultraviolet radiation, and heat or enzyme is described. The method produces gelatin-sugar hydrogels demonstrating greater thermal stability, mechanical strength, and resistance to enzymatic degradation. The invention also provides a means to assemble the gelatin sugar hydrogel films into complex three-dimensional structures (scaffolds). To account for the native biochemical factors present in natural scaffolds, methods of conjugating such factors to the gelatin-sugar hydrogel are described. These scaffolds can then be applied for tissue culturing and organ growth. The present invention also describes a system and apparatus for constructing these complex three-dimensional scaffolds by taking advantage of the physical and chemical properties of the gelatin-sugar hydrogel.

15 Claims, 17 Drawing Sheets

(56) References Cited

OTHER PUBLICATIONS

Liu, CZ, Xia, ZD, Han, ZW, Hulley, PA, Triffitt, JT, Czernuszka, JT (2007). Novel 3D collagen scaffolds fabricated by indirect printing technique for tissue engineering. J. Biomed. Mater. Res. Part B: Appl. Biomater. 85(2): 519-528.
Glowacki J, Mizuno S (2007). Collagen scaffolds for tissue engineering. Biopolymers. 89(5): 338-44.
Hulmes DJS, Miller A (1979) Quasi hexagonal molecular packing in collagen fibrils. Nature 282: 878-880.
Prockop DJ, Feralta A (1998) The collagen fibril; the almost crystalline structure. J. of Structural Biol. 122: 111-118.
Kadler KE, Homes DF, Trotter JA (1996) Collagen fibril formation. Biochem J. 316: 1-11.
Hulmes DJS, Miller A, Parry DAD, Piez KA, Woodhead-Galloway J (1973) Analysis of the primary structure of collagen for the origins of molecular packing. J. Molecular Biol. 79: 137-148.
Hsu S, Jamieson AM, Blackwell J (1994) Viscoelastic studies of extracellular matrix interactions in a model native collagen gel system. Biorheology 31: 21-36.
Lynn AK, Yannas IV, Bonfield W (2004) Antigenicity and immunogenicity of collagen. J. Biomed. Mater. Res. B. Appl. Biomater. 71B: 343-354.
Zeugolis DI, Khew ST, Yew ESY, Ekaputra AK, Tong YW, Yung L-YL, Hutmacher DW, Sheppard C, Raghunath M (2008) Electo-spinning of pure collagen nano-fibres—just an expensive way to make gelatin? Biomaterials 29: 2293-2305.
Veis A, Anesey J, Cohen J (1961). The long range reorganization of gelatin to the collagen structure. Arch. of Biochem. Biophys. 94: 20-31.
Fassina L, Saino E, Visai L, Avanzini MA, Cusella De Angelis MG, Benazzo F, Van Vlierberghe S, Dubruel P, Magenes G (2010) Use of a gelatin cryogel as biomaterial scaffold in the differentiation process of human bone marrow stromal cells. Conf. Proc. IEEE. Eng. Med. Biol. Soc. 2010:247-250.
Ponticiello MS, Schinagl RM, Kadiyala S, Barry FP (2000) Gelatin based resorbable sponge as a carrier matrix for human mesenchymal stem cells in cartilage regeneration therapy. J. Biomed. Mater. Res. 52(2): 246-255.
Ratanavaraporn J, Damrongsakkul S, Sanchavanakit N, Banapreasert T, Kanokpanont S (2006) Comparison of gelatin and collagen scaffolds for fibroblast cell culture. J. Metals, Materials Minerals. 16(1): 31-36.
Sachlos E, Czernuszka JT (2003). Making tissue engineering scaffolds work. Review: the application of solid freeform fabrication technology to the production of tissue engineering scaffolds. Eur. Cell. Mater. 5: 29-39; discussion: 39-40.
Das. S, Pati F, Chameettachal S, Pahwa S, Ray AR, Dhara S, Ghosh S (2013) Enhanced redifferentiation of chondrocytes on microperiodic silk/gelatin scaffolds: Toward tailor-made tissue engineering. Biomacromolecules. In press.
Hunger PM, Donius AE, Wegst UG (2013) Structure-property-processing correlation in freeze cast composite scaffolds. Acta Biomater. In press.
Huang Y, Onyeri S, Siewe M, Moshfeghian A, Madihally SV (2005) In vitro characterization of chitosan-gelatin scaffolds for tissue engineering. Biomaterials 26(36) 7616-7627.
Cortesi R, Nastruzzi C, Davis SS (1998) Sugar cross-linked gelatin for controlled release: microspheres and discs. Biomaterials 19(18): 1641-1649.
Easa AM, Armstrong HJ, Mitchell JR, Hill SE, Harding SE, Taylor AJ (1996) Maillard induced complexes of bovine serum albumin—a dilute solution study. Int. J. Biol. Macromol. 18(4) 297-301.
Lederer MO, Gernum F, Severin T (1998) Cross linking of proteins by Maillard processes-model reaction of D-glucose of methylglyoxal with butylamine and guanidine derivatives. Bioorg. Med. Chem. 6(7): 993-1002.
Nakajima K, Sato M, Hattori M, Yoshida T, Yoshimura K, Takahashi K (2008) Soft textural and emulsifiable gelatin formed by conjugating with fatty-acylated saccharide. Biosci. Biotechnol. Biochem. 72(2): 295-302.
Su G, Cui C, Ren J, Yang B, Zhao M (2011) Effect of xylose on the molecular and particle size distribution of peanut hydrolysate in Maillard reaction system. J. Sci. Food Agic. 91(13): 2457-2462.
Ohan MP, Weadock KS, Dunn MG (2002) Synergistic effects of glucose and ultraviolet irradiation on the physical properties of collagen. J. Biomed. Mater. Res. 60(3): 384-391.
Goldin A, Beckman JA, Schmidt AM, Creager, MA (2006). Advanced glycation end products: sparking the development of diabetic vascular injury. Circulation 114(6): 597-605.
Tomihata K, Burczak K, Shiraki K, Ikada Y (1994) Cross-Linking and Biodegradation of Native and Denatured Collagen. In: Shalaby SW, Ikada Y, Langer R, Williams J, editors. Polymers of Biological and Biomedical Significance. American Chemical Society. Chapter 24; 275-286.
Schuler B (2004) Evaluation of Novel Cross-linking Agents for Gelatin/Collagen Matrices. PhD dissertation, School of Pharmacy at West Virginia University. 279 p.
Weadock KS, Miller EJ, Bellincampi LD, Zawadsky JP, Dunn MG (1995). Physical crosslinking of collagen fibers: comparison of ultraviolet irradiation and dehydrothermal treatment. J. Biomed. Mater. Res. 29(11): 1373-1379.
Fujimori E (1965) Ultraviolet light-induced change in collagen macromolecules. Biopolymers. 3: 115-119.
Cooper DR, Davidson RJ (1965) The effect of ultraviolet irradiation on soluble collagen. Biochem. J. 97: 139-147.
Miskon A, Ehashi T, Mahara A, Uyama H, Yamaoka T (2009) Beating behavior of primary neonatal cardiomyocytes and cardiac-differentiated P19.CL6 cells on different extracellular matrix components. J. Artif. Organs 12(2): 111-117.
Waksman BH, Mason HL (1949) The Antigenicity of Collagen. J. Immunol, 63:427-433.
Miyahara T, Murai A, Tanaka T, Shiozawa S, Kameyama M (1982) Age-related differences in human skin collagen: solubility in solvent, susceptibility to pepsin digestion, and the spectrum of the solubilized polymeric collagen molecules. J. Gerontol. 37(6): 651-655.
Eastoe E (1955). The Amino Acid Composition of Mammalian Collagen and Gelatin. Biochem. J. 61(4): 589-600.
Vaid FHM, Shaikh RH, Ansari IA, Ahmad I (2005). Spectral Study of the Photolysis of Aqueous Thiamine Hydrochloride and Ascorbic Acid Solutions in the Presence and Absence of Riboflavin. J. Chem. Soc. Pak. 27(3): 227-232.
Brand-Williams W, Cuvelier ME, Berset C (1994). Use of a Free Radical Method to Evaluate Antioxidant Activity. LWT-Food Sci. Technol. 28(1): 25-30.
Gill SC, von Hippel PH (1989). Calculation of Protein Extinction Coefficients from Amino Acid Sequence Data. Anal. Biochem. 182(2): 319-326.
Ishimitsu S, Fujimoto S, Ohara A (1990). Tyrosine Formation from Phenylalanine by Ultraviolet Irradiation. Chem. Pharm. Bull. 38(5): 1417-1418.
Lundblad RL, MacDonald FM (2010). Handbook of Biochemistry and Molecular Biology, 4th edn. Chemical Rubber Company Press, Cleveland, OH, pp. 81.
Jin F, Leitich J, von Sonntag C (1995). The photolysis ($\lambda$=254 nm) of tyrosine in aqueous solutions in the absence and presence of oxygen. The reaction of tyrosine with singlet oxygen. J. Photochem. Photobiol. A: Chem. 92: 147-153.
Rosei MA, Coccia R, Blarzino C, Foppoli C, Mosca L (1995). The oxidation of oxytocin and vasopressin by peroxidase/H2O2 system. Amino Acids. 8: 385-391.
Sionkowska A, Skopinska J, Wisniewski M, Leznicki A, Fisz J (2006). Spectroscopic studies into the influence of UV radiation on elastin hydrolysates in water solution. J. Photochem. Photobiol. B: Biol. 85: 79-84.

(56) References Cited

OTHER PUBLICATIONS

Felder T, Bogengruber E, Tenreiro S, Ellinger A, Sa-Correia I, Briza P (2002). Dtr1p, a Multidrug Resistance Transporter of the Major Facilitator Superfamily, Plays an Essential Role in Spore Wall Maturation in Saccharomyces cerevisiae. Eukaryot. Cell. 1(5): 799-810.

Hollister SJ (2005). Porous scaffold design for tissue engineering. Nat. Mater. 4: 518-524.

Tiwari A. and Hihara L.H. (2012) Effect of inorganic constituent on nanomechanical and tribological properties of polymer, quasi ceramic and hybrid coatings. Surface and coatings tech. 206: 4606-4616.

* cited by examiner

```
┌─────────────────────────────────────────────────────────────────────────┐
│   Determine individual cross-section patterns to construct desired 3D   │
│            scaffold from individual GSH sheets (CU)                     │
└─────────────────────────────────────────────────────────────────────────┘
                                    ↓
┌─────────────────────────────────────────────────────────────────────────┐
│   Print UV blocking material on unwanted areas of GSH sheets according  │
│       to cross-section patterns determined in previous step (PU1)       │
└─────────────────────────────────────────────────────────────────────────┘
                                    ↓
┌─────────────────────────────────────────────────────────────────────────┐
│ Irradiate sheets with UV radiation to promote cross-linking in unmasked │
│              regions to alter material properties (PU1)                 │
└─────────────────────────────────────────────────────────────────────────┘
                                    ↓
┌─────────────────────────────────────────────────────────────────────────┐
│  Print select biochemical factors to modulate select cellular processes │
│   onto GSH layers according to cross-section patterns determined in     │
│    step 1. Crosslink biochemical factors to the GSH layers. Locally     │
│             apply thermal irradiation to modulate stiffness (PU2)       │
└─────────────────────────────────────────────────────────────────────────┘
                                    ↓
┌─────────────────────────────────────────────────────────────────────────┐
│            Remove masked regions of sheets with hot solvent (PU3)       │
└─────────────────────────────────────────────────────────────────────────┘
                                    ↓
┌─────────────────────────────────────────────────────────────────────────┐
│  Align and stack sheets to form 3D scaffold and fuse sheets using sugar │
│                      solution and heat or enzyme (PU4)                  │
└─────────────────────────────────────────────────────────────────────────┘
                                    ↓
┌─────────────────────────────────────────────────────────────────────────┐
│    Locally perfuse GSH stack with select biochemical factors to modulate│
│    select cellular processes according to cross-section patterns        │
│    determined in step 1. Crosslink biochemical factors to the GSH       │
│                            layers (PU5)                                 │
└─────────────────────────────────────────────────────────────────────────┘
```

FIG. 2

4a.
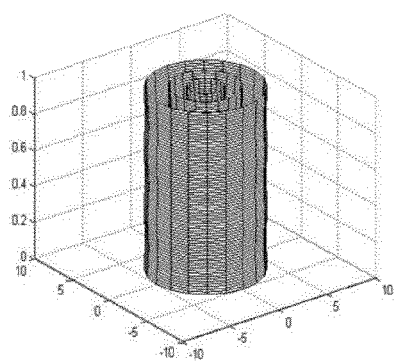
4b.
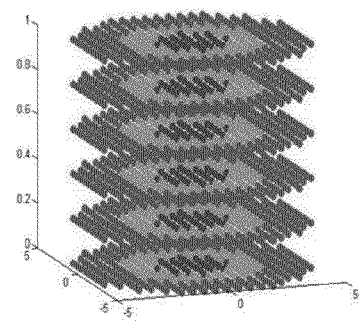
4c.
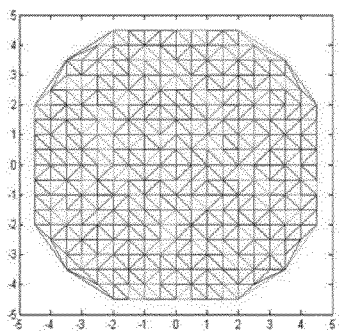
4d.
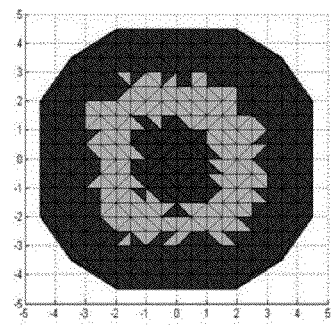
FIG. 4

| GEL COMPOSITION | MEAN YOUNG'S MODULUS (GPa) | STANDARD DEVIATION (GPa) |
| --- | --- | --- |
| +glucose/-UV | 3.45 | 0.68 |
| +glucose/+UV | 3.38 | 0.71 |
| -glucose/-UV | 21.00 | 10.70 |
| -glucose/+UV | 17.56 | 8.96 |

FIG. 22

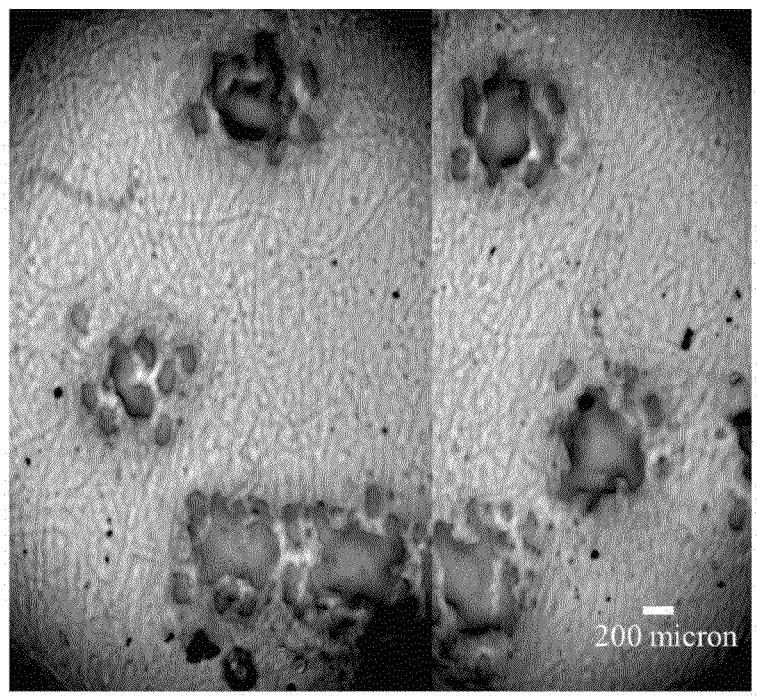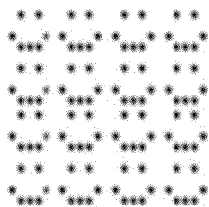
FIG. 23

METHODS AND APPARATUS FOR BUILDING COMPLEX 3D SCAFFOLDS AND BIOMIMETIC SCAFFOLDS BUILT THEREFROM

CROSS-REFERENCE TO RELATED APPLICATIONS

This U.S. Non-Provisional Utility Patent Application claims the benefit, under 35 U.S.C. §119, of U.S. Provisional Patent Application No. 61/763,450, filed Feb. 11, 2013, and U.S. Provisional Patent Application No. 61/780,802, filed Mar. 13, 2013, the contents of which are incorporated herein by this reference in their entireties.

FIELD OF THE INVENTION

The present invention is in the technical field of biological materials. More particularly, the present invention describes the methods and apparatus employed to construct biomimetic scaffolds for cell culture.

BACKGROUND OF THE INVENTION

Pursuit of in vitro biomimetic organ growth has spurred a number of recent investigations of methods to generate three-dimensional (3D) scaffolding structures and techniques for cellular seeding (Schmeichel K L and Bissell M J. (2003) J. Cell Sci. 116:2377-2388; Cukierman et al. (2001) Science 294:1708-1712; Tsang V L and Bhatia S N. (2006) Adv. Biochem. Eng. Biotechnol. 103:189-205). In vitro organs that have demonstrated functionality similar to natural organs have been produced previously by cell re-seeding onto cadaver-derived, de-cellularized protein scaffolds (Ott et al. (2010) Nat. Med. 16:927-933). These results suggest that the development of a sufficiently complex 3D cell scaffold may allow for the re-growth of organs de novo.

Cell scaffolding structures, commonly referred to as extra-cellular matrices (ECM), should be constructed from benign compounds (Owen S C and Schoichet M S. (2010) Biomed. Mater. Res. A 94:1321-1331). Scaffold materials will either decompose metabolically during cell propagation or be fully incorporated into the final organ. Materials that have been suggested include ceramics, chitosan, collagen, peptides, polyethylene glycol (PEG), polysaccharides, and various synthetic biomaterials (Bartolo et al. (2011) Advances on Modeling in Tissue Engineering. Dordrecht: Springer Netherlands, pp. 137-176). For applications involving human hosts, material selection criteria must consider toxicity, antigenicity, mechanical strength, thermal stability, and porosity.

Collagen has been used frequently in previous investigations of ECM development (Bartolo et al. (2011) Advances on Modeling in Tissue Engineering. Dordrecht: Springer Netherlands, pp. 137-176; Liu et al. (2007) J. Biomed. Mater. Res. Part B 85:519-528; Glowacki J and Mizuno S (2007) Biopolymers 89:338-344). It is a crystalline (Hulmes D J S and Miller A (1979) Nature 282:878-880; Prockop D J and Feralta A (1998) J. Struct. Biol. 122:111-118; Kadler er al. (1996) Biochem. J. 316:1-11), triple helical molecule (Hulmes et al. (1973) J. Molecular Biol. 79:137-148) and a favorable material for biomedical applications, since it is a biodegradable and biocompatible, insoluble fibril with high mechanical strength and relatively low immunogenicity (Hsu et al. (1994) Biorheology 31:21-36; Lynn et al. (2004) J. Biomed. Mater. Res. B Appl. Biomater. 71B:343-354; Zeugolis et al. (2008) Biomaterials 29:2293-2305).

Gelatin is the incompletely denatured form of collagen and comprises variable-length peptides which have fibrillar structure but lack configurational order (Veis et al. (1961) Arch. Biochem. Biophys. 94:20-31). In vivo use of gelatin has been successfully demonstrated by implantation in animal models, with results that suggest low toxicity and reduced antigenicity relative to collagen (Fassina et al. (2010) Conf. Proc. IEEE Eng. Med. Biol. Soc. 2010:247-250; Ponticiello et al. (2000) J. Biomed. Mater. Res. 52:246-255). Furthermore, gelatin is relatively inexpensive compared to collagen and its cell adhesion and proliferation characteristics are essentially indistinguishable (Ratanavaraporn et al. (2006) J. Metals Materials Minerals 16:31-36). Gelatin's use in ECM is complicated by its lack of 3D structural integrity, lower melting temperatures, and rapid dissolution in water (Veis et al. (1961) Arch. Biochem. Biophys. 94:20-31; Sachlos E and Czernuszka J T (2003) Eur. Cell. Mater. 5:29-40). For use as cell scaffolds, recent studies have sought to increase the mechanical and thermal resiliency through compositing with various compounds (Das et al. (2013) Biomacromolecules 14(2):311:321; Hunger et al. (2013) Acta. Biomater. 9(5):6338-6348) and by utilization of covalent cross-linking agents (Huang et al. (2005) Biomaterials 26:7616-7627). Many cross-linking agents, however, are toxic or immunogenic, e.g., glutaraldehyde (Glowacki J and Mizuno S (2007) Biopolymers 89:338-344).

The utilization of sugars as a gelatin cross-linking agent has been previously investigated (Cortesi et al. (1998) Biomaterials 19:1641-1649), and its usefulness in vivo without host toxicity successfully demonstrated. Cross-linking between gelatin and both non-reducing and reducing sugars can be observed without catalysis; however, due to weak ionic interactions, dissolution still occurs at physiological temperatures (lower than 37° C.), albeit at a reduced rate (Cortesi et al. (1998) Biomaterials 19:1641-1649). The formation of covalent interactions is therefore necessary to produce a thermo-stable compound. The Maillard reaction pathway generates covalent bonds between reducing sugars and protein amine groups (Easa et al. (1996) Int. J. Biol. Macromol. 18:297-301) and produces observable physical changes in gelatin and other protein matrices (Lederer et al. (1998) Bioorg. Med. Chem. 6:993-1002; Nakajima et al. (2008) Biosci. Biotechnol. Biochem. 72:295-302; Su et al. (2011) J. Sci. Food Agric. 91:2457-2462).

Glycation end products are the resultant glycosylated proteins generated by Maillard chemistry (Ohan et al. (2002) J. Biomed. Mater. Res. 60:384-391; Goldin et al. (2006) Circulation 114:597-605). Sugar cross-linking of gelatin molecules has been shown to increase stiffness and decrease solubility (Goldin et al. (2006) Circulation 114:597-605; Tomihata et al. (1994) Polymers of Biological and Biomedical Significance. American Chemical Society. Chapter 24, 275-286). As demonstrated quantitatively herein, ultraviolet (UV) radiation can provide the necessary energetic input required to crosslink gelatin. The cross-linked gelatin product exhibits good thermal stability and has the potential for future 3D cell scaffold application.

SUMMARY OF THE INVENTION

The present invention describes methods for the simultaneous cross-linking and patterning of gelatin and sugar hydrogels on a very fine scale using UV radiation, followed by heat treatment. Another aspect of the present invention is biomimetic scaffolds made with the described methods. A further variant of the present invention is apparatus which employ the method of the present invention to fabricate a 3D gelatin, sugar, and water hydrogels (GSH) structure that can serve as a biomimetic scaffold, comprising some or all of the following steps: 1) computationally dividing a 3D structure into 2D sheets; 2) selectively irradiating individual GSH sheets using UV light according to the pre-computed patterns from step 1; 3) optionally applying desired factors to the GSH sheets to promote cellular processes and selectively applying thermal radiation to locally modulate GSH stiffness; 4) aligning and stacking the individual irradiated sheets; 5) processing the irradiated GSH sheets with solvent to remove areas of non-irradiated material; 6) aligning and stacking the processed sheets; 7) applying a separate cross-linking method to fuse the sheets together; and 8) optionally applying desired factors to the GSH material of the 3D object to help promote cellular processes.

Herein, the synthesis and characterization of the GSH will be discussed, followed by the apparatus utilized to generate useful 3D structures therefrom.

Methods for Making Biometric Scaffolds

According to a preferred embodiment of a method of the subject invention, a 3D-object is sourced from drafting/CAD software or from existing data, e.g., MRI, CT data. A novel program then prepares a map of the different tissue types present in the object by means of an appropriate algorithm which may function generally as follows: The user inputs a desired layer thickness into the program. The program then divides the 3D-object into a series of 2-dimensional (2D) layers with thickness specified by the user. Finally, the program determines the spatial distribution of tissue types on each 2D-layer.

A homogeneous GSH mixture (i.e., a GSH of gelatin, sugar, and water in various proportions, including, optionally, a mixture without a sugar component) is then blended together and maintained in fluid form by the addition of heat. The fluid GSH is poured onto a surface or mold, is processed to achieve desired thickness and geometry, and is allowed to cool and solidify. The GSH sheet is then subjected to UV irradiation from either a diffuse radiation source, e.g., lamp or light-emitting diode (LED), or a focused beam source, e.g., laser or a diffuse source with the appropriate optical equipment.

If the source is diffuse (e.g., a lamp or LED), then an UV radiation-blocking stencil or mask is placed on the GSH. If the radiation source is a focused beam (e.g., focused from a lamp, focused from an LED, or from a laser), then the beam is directed to trace a pattern on the GSH sheet.

During the UV irradiation process, only the areas of the hydrogel that are exposed to the radiation are reacted, resulting in greater thermal stability. The GSH sheet is then checked to determine if it has been sufficiently irradiated. If the GSH sheet is not sufficiently irradiated, then the GSH sheet is additionally exposed to further UV radiation. If the GSH sheet is sufficiently irradiated, then the process proceeds as follows.

To assist in cellular processes not limited to proliferation, differentiation, and localization, the appropriate biochemical factors are applied to the individual sheets through coating and/or perfusion and are subsequently ligated to the GSH sheets. To assist in cellular processes not limited to proliferation, differentiation, and localization, thermal radiation is applied locally to the GSH sheets to locally modulate stiffness. In some embodiments, this process can take place prior to UV irradiation. This step is optionally applied later, as described below, particularly if the biochemical factors to be applied are likely to break down during the heating/fusing step.

Next, the irradiated GSH sheets are aligned and stacked as necessary. In some cases, it is advantageous to temporarily attach the individual sheets together. Next, the irradiated GSH material is immersed in warm (above native gelatin melting point) solvent to remove non-cross-linked gelatin. The remaining non-dissolved GSH material is then collected and dried as necessary.

The processed GSH sheets are next aligned and stacked as necessary. The GSH stacks are then crosslinked together to form bonds between the individual sheets. In one embodiment, the GSH sheets are evenly coated with or immersed in an aqueous solution of reducing sugar(s). These sugar-coated GSH sheets are then stacked and arranged into the desired 3D form.

The stack of GSH sheets is then heated to fuse individual sheets together. Methods of heating include, but are not limited to, thermal irradiation, convective heating, and conductive heating. The resulting GSH stack is then checked to determine if it has been sufficiently heated. If the GSH stack is not sufficiently heated, then the GSH stack is exposed to further heating. If the gel-stack is sufficiently heated, then the fused GSH stack is then rinsed in water to remove excess sugar.

In another embodiment, a catalyst(s) is employed to fuse/form bonds between GSH sheets. One such catalyst is transglutaminase. The GSH sheets are either coated with the catalyst(s) or are immersed in a solution containing the catalyst(s). These catalyst-coated GSH sheets are then stacked and arranged into the desired 3D form. The GSH stack is allowed to incubate under the conditions required by the catalyst. The GSH stack is then subjected to methods to remove or destroy excess catalyst, including but not limited to, rinsing with water, application of catalyst inhibitors, application of chelators, and application of heat.

To assist in cellular processes not limited to proliferation, differentiation, and localization, the appropriate biochemical factors are applied to the individual sheets through coating and/or perfusion and are subsequently ligated to the GSH sheets. In some embodiments as described above, this process can take place prior to the crosslinking between individual sheets particularly, where the biochemical factors are expected to withstand heating or catalytic fusing.

This process improves upon and innovates independent from the current art by, inter alia, 1) the utilization of GSH as a substrate, 2) the use of heated water to selectively dissolve non-irradiated GSH, 3) the synergistic utilization of UV radiation and heating or enzyme to produce the final product, and 4) the local attachment of biochemical factors to modulate cellular processes.

The efficiency of using gelatin, as opposed to collagen, is of particular importance. As mentioned above, gelatin is the product resulting from the hydrolysis/denaturation of collagen. Some differences between gelatin and collagen include that: 1) collagen exists as a triple helix of three subunits, whereas gelatins exist primarily as singular units; 2) gelatin can have a much wider range of molecular weights due to differences in production processes; and 3) gelatin is degraded more easily by proteases in native form relative to collagen (Miskon et al. (2009) J. Artif. Organs 12:111-117). Additionally, while gelatin does not possess antigenicity, collagen elicits an antibody response (Waksman B H and Mason H L (1949) J. Immunol. 63:427-433). Finally, the solubility of collagen in water is extremely low, whereas the solubility of gelatin is very high (Miyahara et al. (1982) J. Gerontol. 37:651-655).

Some of the advantages of using gelatin rather than collagen in the formation of biomimetic scaffolds include: 1) the ability to generate different matrix geometries due to the non-helical nature of gelatin; 2) the development of a protocol for simultaneously sterilizing and denaturing collagen to form gelatin; 3) the ability to modulate enzymatic gelatin degradation by cross-linking; 4) the production of naturally non-antigenic scaffoldings; and 5) the ability to selectively dissolve non-cross-linked gelatin in water. In this fashion, the methods of the present invention can generate biodegradable cell scaffolds for organ growth that will not be rejected upon implantation. Additionally, the described methods impart no toxicity to the final product, which contrasts conventional methods of cross-linking, e.g., application of glutaraldehyde, that leads to toxicity and other complications.

Apparatus for Making Biometric Scaffolds

According to one preferred embodiment, the current invention is an apparatus for fabrication of biometric scaffolds comprising one computational unit and five inter-connected and possibly integrated processing units. The computational unit computes the 2D patterns to be applied to the individual GSH sheets. The first processing unit masks and irradiates the GSH sheets. Thin sheets of GSH, prepared using appropriate proportions of gelatin, sugar, and water, are fed into the first processing unit and are selectively irradiated, according to the predetermined spatial pattern from the computational unit, with UV radiation of a chosen wavelength or wavelengths, intensity, and duration. The selectively irradiated GSH sheets are then transferred from the first processing unit to the second processing unit. The second processing unit selectively applies factors which promote cell processes onto the GSH sheets and applies thermal radiation to locally modulate stiffness on the GSH sheets.

The third processing unit removes areas of non-irradiated and unwanted material. Non-irradiated portions of the GSH sheet, which have a lower melting point and higher solubility in water than the irradiated sections, are removed using heated solvent.

The fourth processing unit aligns and stacks the sheets produced by the third unit into their final 3D configuration, and applies either a sugar solution and heat or a catalyst in the appropriate environment to fuse the individual sheets together.

The fifth and final processing unit then applies additional factors which promote cell processes onto the 3D object and affixes the factors to the GSH material. The described apparatus and system may be automated in whole or in part.

This novel invention exploits the synergistic effects of UV radiation, heat, and biochemical ligation to selectively polymerize, crosslink, and fuse gelatin or GSH to form a complex, 3D structure with the necessary levels of strength, thermal stability, and resistance to dissolution for biomimetic and other related medical, biological, and pharmaceutical applications. The final 3D scaffold also contains biochemical factors required for tissue and organ growth and development.

BRIEF DESCRIPTION OF THE DRAWINGS

FIG. 2 is a schematic diagram/flow chart showing the steps of the production process of the complex 3D scaffold with reference to the apparatus employing the production process.

FIG. 4 are graphs illustrating the action of the computational unit (CU) of the apparatus of the present invention. FIG. 4a. depicts the 3D polygonal mesh of a sample object. FIG. 4b. depicts an example of CU generating a 3D polygon mesh model that identifies the tissue type (signified by different colors) at each point in the mesh. FIG. 4c. depicts an example of a 2D triangle mesh generated by CU, i.e. a 2D triangle mesh slice of 4a. FIG. 4d. depicts the results of assigning a tissue type to each triangular element in 4c.

FIGS. 5 through 23 illustrates results of the experimentation described in the Examples section of this disclosure.

FIG. 5 is a calorimetry graph depicting Heat Rate vs. Temperature (i.e., thermogram) of the completed product and demonstrating the product's thermal stability. Peaks which protrude below the baseline are indicative of endothermic processes, while peaks that protrude above the baseline are indicative of exothermic processes. In particular, melting/fusion is an endothermic process, thus peaks extending below the baseline indicate melting/fusion. Based on this figure, the final product irradiated with UV light undergoes no significant endothermic processes between 20 and 80 degree Celsius, indicating a high level of thermal stability.

FIG. 6 is a photo depicting the GSH material before irradiation. In particular, the pale-yellow color of the sample is noteworthy as explained in the detailed description section below.

FIG. 7 is a photo showing the GSH material following UV irradiation. In particular, the pink-tan color of the sample is noteworthy as explained in the detailed description section below.

FIG. 8 is a photo depicting a sample prepared using the protocols described herein without irradiation and stained with red food coloring at the time of immersion into a beaker of 85 degree C. water. In particular, the sample is visibly present at the bottom of the beaker before any significant heat transfer.

FIG. 9 is a photo showing the sample from FIG. 8 after being immersed for 30 minutes in the 85 degree C. water. In particular, the sample as depicted from FIG. 8 is now completely dissolved in the water, indicative of low thermal stability.

FIG. 10 is a photo depicting a sample prepared using the protocols described and irradiated with UV light and stained with red food coloring at the time of immersion into a beaker of 85 degree C. water. In particular, the sample is visibly present in the beaker, both floating and on the bottom.

FIG. 11 is a photo showing the sample from FIG. 10 after being immersed for 30 minutes in the 85 degree C. water. In particular, the sample is still present after extended heating in water, indicative of high thermal stability.

FIG. 12 is a photo depicting a set of GSH films prepared using the method of the present invention, irradiated with UV light, subsequently fused together through application of reducing sugar and heat (from thermal irradiation) and immersed in water. In particular, the individual layers of the sample are held together without separation, due to the synergistic action of reducing sugar and thermal irradiation. The sample has also turned brown, indicating a high degree of Maillard reaction cross-linking; the yellow color of the water is due to solubilization of Maillard reaction by-products.

FIG. 13 is a photo showing a set of gelatin films prepared using the method of the present invention, irradiated with UV light, and subsequently fused together through selective application of transglutaminase.

FIG. 14 is a photo depicting the GSH stack of FIG. 13 some time after immersion in hot water. In particular, the individual layers of the sample are held together without separation due to the transglutaminase-induced crosslinking.

FIGS. 15 to 18 present photographs that demonstrate proof of concept of step 1 (irradiation of masked GSH sheets) and step 2 (hot water removal of non-irradiated material). The photographs show a sheet of GSH that has been masked using the photoreactive drum and toner from a modified laser printer (FIG. 16), irradiated with a 254 nanometer UV lamp, and immersed in hot water to remove the nonirradiated (i.e., masked) areas of the sheet (FIGS. 17 and 18).

FIGS. 15 and 16 depict steps that take place within processing unit 1. FIG. 15 shows the masking pattern to be applied onto the sheet of GSC with a 50 Yen coin for size comparison. FIG. 16 shows the sheet of GSC with masking pattern applied.

FIGS. 17 and 18 illustrate steps that occur within processing unit 3. FIG. 17 shows one view of the sheet of GSC following hot water immersion prior to drying. FIG. 18 shows another view of the sheet of GSC following hot water immersion and after drying.

FIG. 12 shows an example of the result of multiple sheets of GSC fused together through the application of heat and reducing sugar within processing unit 4.

FIG. 14 shows an example of the result of multiple sheets of GSH fused together through the application of enzyme (transglutaminase) within processing unit 4.

FIG. 19 shows the scanning electron microscopy (SEM) comparisons of irradiated samples to non-irradiated samples: FIGS. 19A, 19C and 19E being of irradiated samples; and FIGS. 19B, 19D and 19F, being of non-irradiation samples.

FIG. 20 shows SEM comparisons of lyophilized (i.e., freeze-dried) irradiated samples to lyophilized non-irradiated samples: FIG. 20A shows a non-irradiated lyophilized sample. Note the smooth surface and densely-packed cross-section; FIGS. 20B and 20C show irradiated lyophilized samples. Note the increased density near the surface; FIG. 20D shows an irradiated lyophilized sample surface. Note the fibrillar, pockmarked pattern.

FIG. 21 shows the UV-Visible transmittance spectra for irradiated and non-irradiated gels. The red spectrum is that of the irradiated sample, while the blue spectrum is that of the non-irradiated sample. UV irradiation imparts significantly reduced transmittance from ~250-375 nm and between ~375-550 nm.

FIG. 22 displays the nano-indentation Young's Modulus data for gels with or without glucose and with or without UV irradiation.

FIG. 23 shows the selective irradiation of gels through application of ascorbic acid solution. FIG. 23A depicts the resultant pattern after immersion in hot water under 40× magnification. FIG. 23B depicts the original computer-generated pattern.

DETAILED DESCRIPTION OF THE INVENTION

Described in detail below are preferred embodiments of novel methods and apparatus to crosslink gelatin for the development of a suitable cell scaffold material that employ UV radiation and/or heat and/or enzymes as necessary inputs for the catalysis of gelatin-sugar mixtures, and the biomimetic scaffold products made from the novel methods. The following detailed description first covers the methodology of 3D scaffold formation, and subsequently describes the apparatus employed to accomplish synthesis of the 3D scaffold.

Detailed Description of the Methods of the Invention

Figure 1:
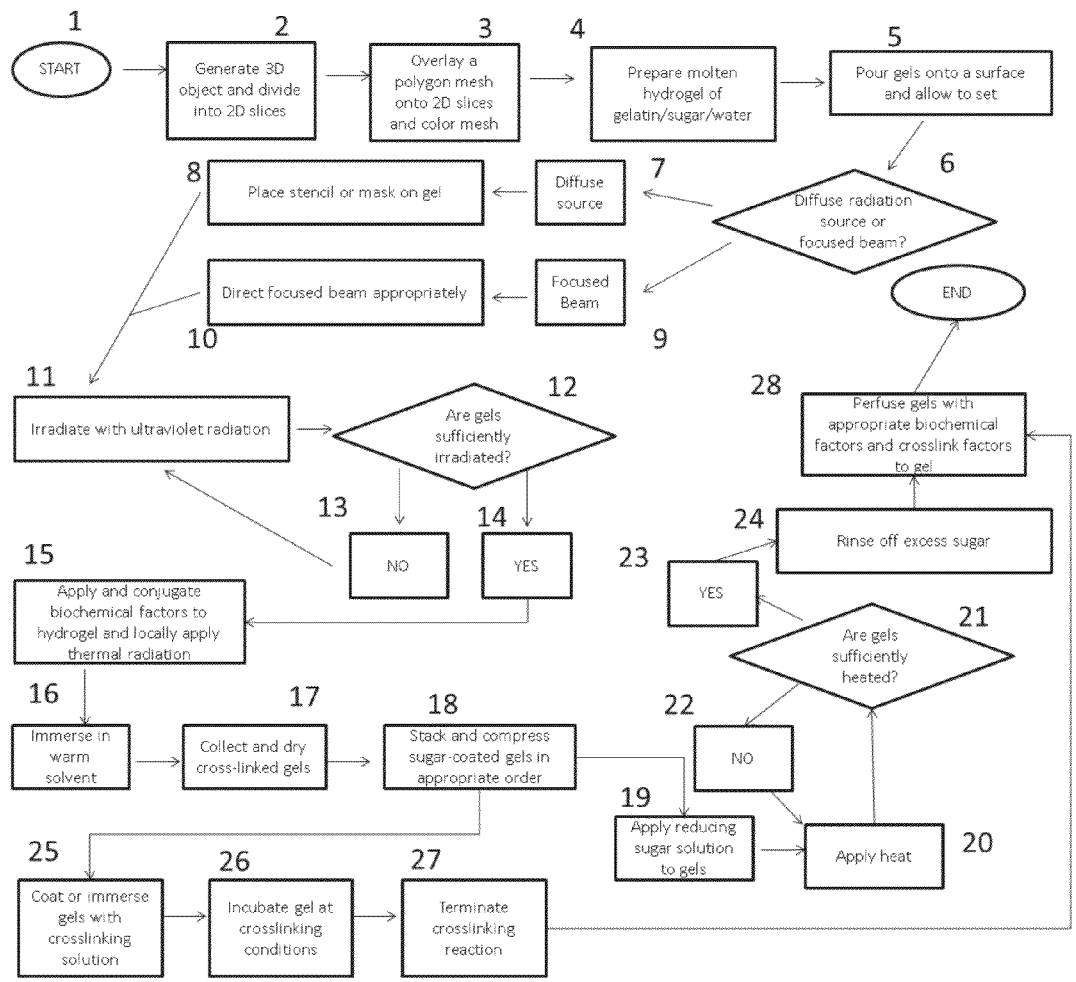
FIG. 1 is a flowchart illustrating the steps required to synthesize the biomimetic scaffolds according to the method of the present invention.

Methods of the instant invention are illustrated generally with respect to the flowchart depicted in FIG. 1, with the numbers adjacent to each circle, rectangle or diamond enclosure referring the step numbers described herein.

The desired 3D scaffold is generated by a program and is divided into 2D layers (step 2). Different features, including but not limited to: empty space, tissue type, and cell density, are assigned to locations on these layers (step 3).

Next, a homogeneous GSH of gelatin, sugar (optional), and water (hereinafter referred to interchangeably as "GSH" or "gel") is blended together and maintained in fluid form by the addition of heat (step 4). The fluid GSH material is poured onto a surface or mold and is allowed to cool and solidify (step 5).

The resulting GSH sheet is then subject to UV irradiation (steps 6 to 11) from either a diffuse radiation source, e.g. lamp or light emitting diode (LED) (step 7), or a focused beam source, e.g., laser or a diffuse source with the appropriate optical equipment (step 9). If the source is diffuse (e.g., a lamp or LED), then an UV radiation-blocking and/or free-radical neutralizing stencil or mask is placed on the surface of the GSH sheet (step 8). If the radiation source is a focused beam (e.g., focused from a lamp, focused from an LED, or from a laser), then the beam is directed to trace a pattern on the GSH sheet (step 10).

The GSH sheet is then irradiated with UV light (step 11), and only the regions exposed to the UV radiation are reacted, resulting in greater thermal stability. In some embodiments, it is advantageous to irradiate the GSH in a sealed environment with known gaseous components. Particularly, modulation of diatomic oxygen concentrations can alter crosslinking penetrance and GSH chemical composition.

The GSH material is then checked to determine if it has been sufficiently irradiated (step 12). If the GSH material is not sufficiently irradiated (step 13), then the GSH is additionally exposed to further UV radiation (steps 6 through 11). If the GSH material is sufficiently irradiated (step 14), then the process proceeds.

In some embodiments, it is advantageous to conjugate factors which promote cellular processes onto the GSH before removal of non-irradiated GSH sections of the sheets (step 15). If applied at this step, the factors should be able to withstand the conditions employed to remove the non-irradiated GSH sections, including but not limited to temperature and solvent composition. Methods to conjugate such factors include, but are not limited to: application of UV radiation and/or application of catalyst (e.g., enzymes such as transglutaminase). In some embodiments, it is also advantageous to locally modulate stiffness of each GSH sheet by locally applying thermal radiation (step 15).

The irradiated GSH material from step 15 is then immersed in warm (above native gelatin melting point) solvent to remove non-crosslinked gelatin (step 16). In some embodiments, the solvent composition is water, whereas in other embodiments, it is advantageous to add additional components to aid non-irradiated gelatin dissolution or to protect conjugated factors. Such components include but are not limited to: acid, base, salt, free-radical scavengers, chelators, and catalysts.

The remaining non-dissolved solid GSH material is next collected and dried as necessary (step 17). These GSH pieces are then stacked and arranged into the desired 3D form (step 18). Depending on the desired final properties of the gel, in one embodiment the dried GSH material is evenly coated with, or immersed in, an aqueous solution of reducing sugars(s) (step 19).

The stack is then heated to fuse the individual gels together (step 20). Methods of heating include, but are not limited to, thermal irradiation, convective heating, and conductive heating. The stack is then checked to determine if it has been sufficiently heated (step 21). If the stack is not sufficiently heated (step 22), then the stack is exposed to further heating. If the stack is sufficiently heated (step 23), then the process proceeds.

The fused stack is next rinsed in water to remove excess sugar (step 24).

In another embodiment, the dried GSH stack from step 18 is evenly coated with, or immersed in, a crosslinking solution (step 25). The components of the crosslinking solution can include, but are not limited to, transglutaminase and other enzymatic crosslinkers. The coated GSH stack is then incubated at the conditions required for crosslinking (step 26). At the end of incubation, crosslinking is terminated through methods which include, but are not limited to, rinsing, applying inhibitor, and exposing to temperature changes (step 27).

After the GSH layers have been crosslinked to each other (either step 24 or step 27), the resulting GSH stack is perfused locally with the appropriate biochemical factors to modulate select cellular processes (step 28). These factors are then conjugated to the GSH stack. In some embodiments, it is more convenient to conduct the action of step 28 after step 18 as, for example, where the conjugated factors are expected to withstand the steps (18 through 27) required to fuse the irradiated GSH sheets.

Selected steps of preferred embodiments of the methods of the invention are described in additional detail while still referring to FIG. 1.

The preparation of the GSH material (step 4) is largely dependent on the qualities desired from the resulting irradiated GSH. Differing proportions of gelatin, sugar, and water will yield different properties including, but not limited to, varying tensile strength, varying degrees of swelling in water, and varying thermodynamic profiles. It is also possible to apply lyophilization (i.e. freeze-drying which will draw out all the moisture from the gel) to the GSH either before or after irradiation (step 11) to yield porosity or to dehydrate the GSH.

Still referring to the invention of FIG. 1, the surface of the mold utilized (in step 5), onto which the GSH material is poured, will affect the nature of the final product. Specifically, the degree of roughness or porosity of the mold surface will influence the surface geometries of GSH sheets, i.e., the surface of the GSH sheets will be imprinted by the mold surface and will retain that form.

Still referring to the invention as illustrated in FIG. 1, the decision of whether to use an LED, lamp, or laser UV radiation source will not greatly impact the physical properties of the final product; however, the two sources require two very different setups. In the case of a lamp or LED or other diffuse radiation source (step 7), the production of many UV light-blocking stencils or masks is required. In one embodiment, a photomask comprising an aqueous solution of ascorbic acid has been shown to work. In the case of a focused beam (step 9), a means of directing the beam or the GSH is required. Another possibility is the use of a fiber optic from either a lamp or LED or beam source in conjunction with an automated directing system to selectively irradiate the gels.

Still referring to the invention of FIG. 1, the resulting product (step 14) has substantially different physical properties relative to non-irradiated GSH material (step 5) and is frequently accompanied by a color change during irradiation (step 11), typically changing from pale yellow to pink. Determining whether sufficient UV irradiation has occurred (step 14), depends primarily on the desired characteristics of the final GSH product and of the process itself, but a good indicator of sufficient UV irradiation (step 12) is a visibly pink GSH material. More total UV irradiation will yield greater cross-linking in the GSH material. Longer UV irradiation times or greater UV radiant intensity is required to penetrate deeper into the GSH material.

Another method to increase the depth from the surface exposed to UV light over which significant crosslinking occurs is to alter the composition of the gaseous environment surrounding the GSH material during irradiation. Specifically, removal or displacement of diatomic oxygen with inert gas, e.g., argon, will increase this depth. The different properties imparted by greater cross-linking include, but are not limited to, greater thermal stability, greater tensile strength, and greater resistance to enzymatic attack.

Still referring to the invention of FIG. 1, the application of biochemical factors to the individual GSH sheets (step 15) is meant to aid in achieving the desired final cellular configuration. Specifically, the action of these factors can include, but are not limited to, localization of specific cell types, alteration of cellular proliferation, and differentiation of immature cells into pre-determined cell types. Examples of such factors include, but are not limited to, growth factors, integrin antigens, and tissue debris. These factors should be able to withstand the physical and chemical stresses that occur in subsequent steps of the process (e.g., step 16 and step 20), including but not limited to, temperature and pH changes. If they cannot, the application of these factors is deferred until later in the process. If the factors are to be applied, the factors are conjugated to the GSH surface through methods which will not disrupt factor function. Such conjugation methods include, but are not limited to, application of transglutaminase or application of photosensitizer and exposure to UV radiation.

Still referring to the invention of FIG. 1, the local application of thermal radiation to the individual GSH sheets (step 15) is meant to locally modulate the stiffness of each GSH to aid in achieving the desired final cellular configuration. Specifically, local stiffness can influence stem cell fate (Engler et al. (2006) Cell 126(4):677-689).

Still referring to the invention of FIG. 1, the immersion of the irradiated GSH material in warm solvent (step 16) serves to selectively dissolve non-irradiated sectors of the material. As a result of this dissolution, the GSH material takes the shape as designed and irradiated. This process would be either impossible or very inefficient when using a substrate with limited or no solubility in solvents such as water, e.g., if using collagen. It can be advantageous to alter the composition of the solvent to protect the conjugated factors or to accelerate the rate of non-irradiated GSH dissolution. Solvent formulation can comprise, but is not limited to, water, oils, detergent, acid, base, and enzymes.

Still referring to the invention of FIG. 1, the collection and drying of damp cross-linked GSH pieces (step 17) requires particular care. As the individual layers of GSH pieces are thin and relatively fragile at this stage, they are easy to damage. Additionally, the pieces have a tendency to fold in on themselves (during step 16). It is advisable to utilize a non-adhesive surface or container when immersing in warm water, e.g., PTFE, in conjunction with a means of clamping down the GSH pieces so that they do not fold in on themselves. A possible means of clamping down the pieces is the application of an electric and/or magnetic field. Magnetic metal should be applied either inside and/or outside the GSH pieces to allow manipulation by the magnetic field. Another possible means to aid immobilization of the damp GSH pieces is to crosslink the edges of the pieces together with UV radiation or transglutaminase. The crosslinked stack of GSH pieces is then clamped down using the methods described above.

The degree of dryness upon entering (step 17) will also affect the properties of the GSH material, not limited to: stiffness, melting point, and strength of bonds between individual pieces.

Still referring to the invention of FIG. 1, the application of a reducing sugar solution to the GSH material (step 19) directly impacts the rate at which the individual GSH pieces polymerize together to form a cohesive object. The choices of reducing sugar as well as concentration of the reducing sugar solution are the two primary factors which affect this rate of polymerization. Using sugars with greater reducing ability and/or at greater concentrations will increase the rate of polymerization (in step 20); sugars with less reducing ability and/or at lower concentrations will polymerize at slower rates.

Still referring to the invention of FIG. 1, the purpose of heating the GSH material (step 20) is to accelerate the glycation and Maillard reactions between gelatin and reducing sugar. As a result, the proteins and sugars chemically react to form strong covalent bonds, ultimately linking the protein-rich GSH pieces together to form the desired 3D product, as well as modulating the overall cross-link density of the final product.

Still referring to the invention of FIG. 1, determining whether the GSH material is sufficiently heated (step 21) depends on the desired qualities of the product. Longer heating times result in a more densely cross-linked product. Increasing cross-linking density increases the mechanical strength and thermal durability of the product and makes the product more resistant to enzymatic degradation. In general, however, sufficient heating can be determined colorimetrically, as the clear and colorless GSH material resulting from (step 16) (the pink color is lost upon immersion in warm water) turns progressively browner with increased heating time. After correlating a particular shade of brown with the desired cross-linking density, the GSH material should be heated until it reaches that shade of brown.

Still referring to the invention of FIG. 1, the application of transglutaminase or other enzyme crosslinker (step 25) is another method to attach the individual 2D GSH pieces together to form a cohesive 3D structure. This method has the advantage of taking place at temperatures significantly lower than those required for the Maillard reaction. Changing the concentration of transglutaminase and the duration of incubation with enzyme (step 26) will alter the final stiffness of the 3D structure. Longer incubation times result in a more densely cross-linked GSH material. Increasing the cross-linking density of the GSH material increases its mechanical strength and resistance to thermal degradation and makes it more resistant to enzymatic degradation.

Once the desired crosslinking density has been achieved, it is advantageous to inactivate or remove excess enzymes/crosslinkers (step 27). Methods of inactivation include, but are not limited to, temperature shock, exposure to oxygen gas, and rinsing with water.

Still referring to the invention of FIG. 1, the application of biochemical factors to the individual GSH sheets (step 28) is meant to aid in achieving the desired final cellular configuration. Specifically, the action of these factors can include, but are not limited to, localization of specific cell types, alteration of cellular proliferation, and differentiation of immature cells into pre-determined cell types. Examples of such factors include, but are not limited to, growth factors, integrin antigens, extracellular matrix material, and tissue debris. These factors should be able to withstand the physical and chemical stresses that occur in subsequent steps of the process, including but not limited to, temperature and pH changes.

Application of factors to the GSH material is more challenging once the GSH pieces have been stacked and arranged to some degree. It is advantageous to solubilize the desired factors, then selectively perfuse the stacks with the desired factors. These factors are then conjugated to the material surfaces of the GSH material through methods which will not disrupt factor function. Such conjugation methods include, but are not limited to, application of transglutaminase or application of photosensitizer and exposure to UV radiation.

The construction details of the invention as illustrated in FIG. 1 include the application of a wide range of sugars that includes monosaccharides, oligosaccharides, polysaccharides, and mixtures thereof. The sources of radiation or heating (steps 6 and 20, respectively) are various, with the only requirement being the emission of UV radiation (e.g., an LED or a mercury lamp or a gas or solid state laser) in step 6 and heat (e.g., an oven or a water bath or a halogen lamp or a gas or solid state laser) in step 20. Only the areas of the GSH material exposed to the radiation and heating or enzyme will react, resulting in the formation of the biometric scaffolds of the present invention.

Detailed Description of the Apparatus Employing the Methods

The following detailed description describes the apparatus utilized for the construction of 3D GSH scaffolds using the methods described previously. The following detailed description is made with reference to FIGS. 2 and 3, a flowchart and schematic diagram showing the steps of the production process of the complex 3D scaffold and production unit apparatus used in the process.

Figure 3:
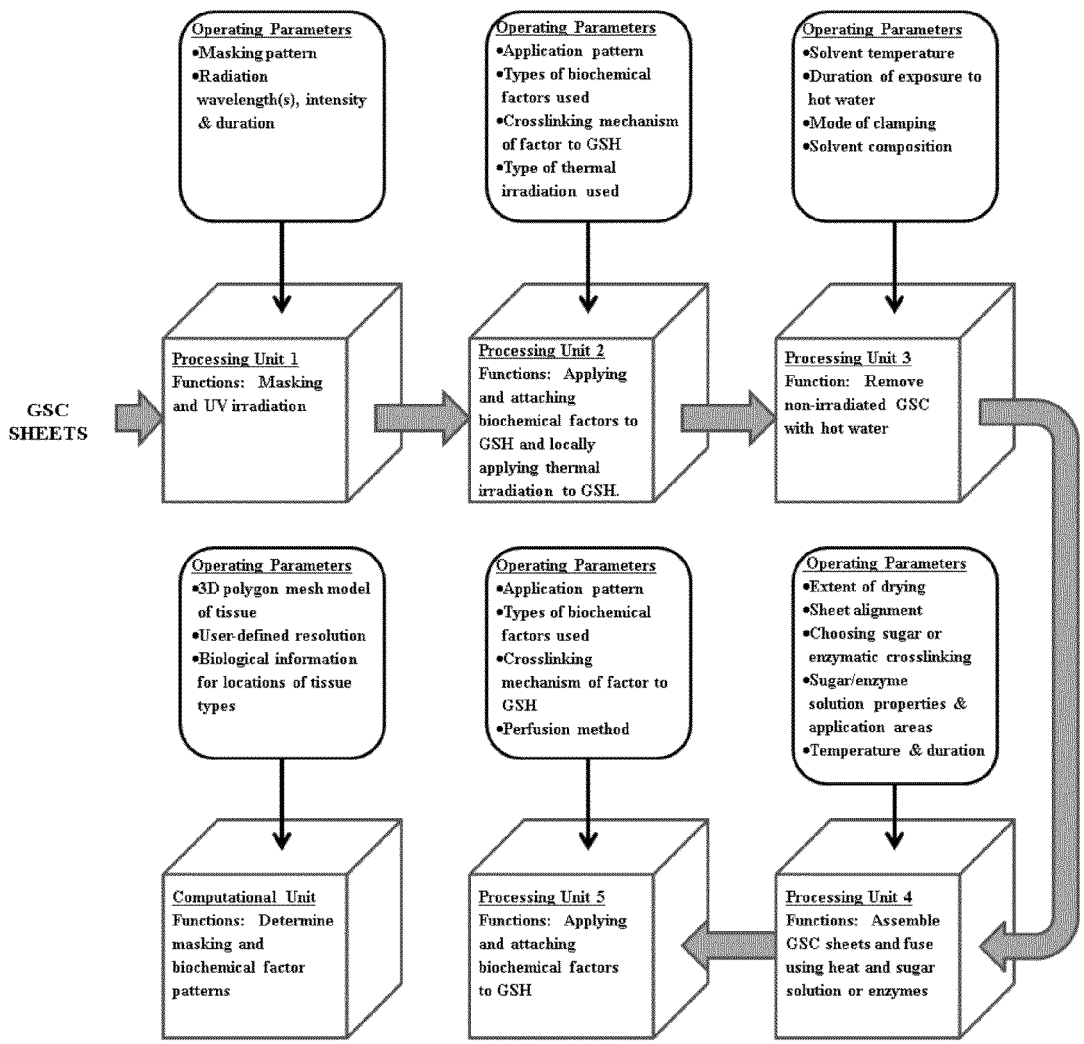
FIG. 3 a conceptual schematic diagram of the method and apparatus of the present invention with the steps and with the computational and processing units represented as "black boxes."

Referring to FIG. 3, a conceptual schematic diagram of the system of the present invention is shown. Individual computational and processing units represented as "black boxes" are included in the diagram to identify primary steps of the production process. In practice, these units may or may not be integrated into a single device or multiple devices in some combinations.

The first unit of the system is a computational unit (CU). The CU develops a 3D model of the biomimetic GSH scaffold, based on user input, that is employed in the production process by the processing units.

The user first provides data to CU. These data are the 3D polygon mesh of the desired object that may consist only of the scaffold or may include other materials (e.g., entire organs or other body parts). These data can be generated from CAD programs or derived from existing measurement data, e.g., MRI and CT data. The user then selects the desired resolution of different tissue types. The knowledge of which tissue type exists at a given 3D location must be sourced from actual measured data. CU then generates a 3D polygon mesh model that identifies the tissue type at each point in the mesh and adjusts local mesh size according to the user-specified resolution.

CU next proceeds to divide the polygon mesh model into printable layers using an appropriate algorithm.

In one possible embodiment, by way of example and not limitation, the algorithm is defined in terms of the following steps: The polygon mesh model is a 3D polyhedron which can be specified by a set of polygonal planar faces. Each planar face is defined by a number of ordered vertices, with neighboring vertices being connected by an edge (line). CU will calculate the smallest cube which contains the imported structure and will divide this cube into a user-specified number of 'slices' by generating a number of equally spaced horizontal planes within the cube, with each plane parameterized by a vertical z-coordinate value. CU then finds the intersection of the planes with the edges specified by the input polygon mesh structure, which will define a 2D-polygon as viewed from above. To find this polygon one takes the list of all edges in the structure and finds the intersection of the plane with the first edge using linear algebra. CU then checks if the intersection is contained in the edge. If it is not, then CU moves on to the next edge in the list until it has found an edge (edge1) which does intersect the plane. CU then finds the edge opposite of edge1 (edge2) and generates a new line segment connecting edge1 and edge2 at the current z-coordinate value in a new list. CU conducts this edge connection iteratively until it reaches the original edge1, forming a closed-loop. CU then exhaustively searches for additional edge intersections with the current plane and iteratively generates closed loops. In this way, the internal features of the polygon mesh are captured as well. CU then looks at the next plane and generates all possible closed loops iteratively. Once all horizontal layers have been generated, the process proceeds.

In order to generate the tissue-type information for the production process, the aforementioned layers are partitioned accordingly. The user specifies a value for the area of a unit square or triangle that lies within an attainable range for the subsequent GSH production steps. Each of the 2D horizontal layers generated in the previous step is divided into a grid comprising the aforementioned unit squares or triangles. CU then utilizes the tissue-type information for the 3D polygon mesh of the object described above to determine the corresponding tissue type for each unit of the grid. In one possible embodiment, CU employs a k-nearest neighbors algorithm to select the appropriate tissue type for each unit based on the tissue-type data of the nearest point in the 3D polygon mesh. This process continues until all unit squares or triangles on all layers are assigned a tissue type. Regions of dead space, e.g. lumen, are also identified for removal during subsequent processing steps. CU also uses experimental data to determine the local stiffness of each square or triangle and assigns locally the amount of thermal radiation required to generate the required amount of stiffness.

FIG. 4 illustrates the functioning of CU in graphical form. FIG. 4a. depicts the 3D polygonal mesh of a sample object. FIG. 4b. depicts an example of CU generating a 3D polygon mesh model that identifies the tissue type (signified by different colors) at each point in the mesh. FIG. 4c. depicts an example of a 2D triangle mesh generated by CU, i.e., a 2D triangle mesh slice of 4a. FIG. 4d. depicts the results of assigning a tissue type to each triangular element in 4c.

Referring to FIGS. 2 and 3, homogeneous sheets of a selected thickness that are composed of gelatin, sugar, and water (GSH sheets) in appropriate proportions are fed individually into a first processing unit (PU1) via an automated transport system, e.g., conveyor belt. The GSH sheet enters PU1, which according to one embodiment comprises a mechanism to apply a coating to mask selected areas on the GSH sheet surface from UV radiation and a UV radiation source to irradiate the sheet for a predetermined period of time at a selected intensity at one or several wavelengths. The mechanism to mask the GSH sheet may consist of a photoreceptive plate or drum and toner such as employed in a laser printer, or a device to apply a precisely-controlled spray of liquid UV-blocking masking material such as employed in an inkjet printer. In a preferred embodiment, the liquid UV-blocking material is a solution of ascorbic acid. Whatever is used will print the masking material onto the GSH sheet surface(s) in a pattern determined by CU for each individual sheet, The masked areas will be protected during the irradiation step and can subsequently be dissolved, either completely or in part, using heat and or/hot water.

The mechanical and thermochemical properties of the final product depend on the hydration and sugar content of the GSH feedstock. Sugars with increasing reducing strength will generally yield high cross-linking density which promotes mechanical and thermal durability. The degree of hydration will inversely affect the density of cross-linking; i.e., cross-linking density decreases as hydration of the GSH increases.

Properties of the masking material (e.g., solid toner particles if a photoreceptive drum approach is employed; or liquid suspension if a spray approach is used) are important. The selected masking material should be non-toxic, non-antigenic, biocompatible, unreactive when exposed to UV or heat, and should be easily removable upon immersion in water. Additionally, this material must be able to block out a significant portion of incident UV radiation.

After completion of the above-described masking or spraying step, and while still in PU1, the GSH sheet is irradiated for a predetermined amount of time at a selected wavelength or wavelengths and radiative intensity, based on the desired properties of the cross-linked GSH material.

The wavelength(s) and power of the UV source is important. The UV source must provide sufficient power at appropriate wavelengths to promote a level of crosslinking over the entire cross section of the gel sheet that is necessary to achieve the desired change in its properties within a reasonable period of time.

The duration and intensity of irradiation will directly affect the properties of the final product: duration of irradiation generally is proportional to the degree of cross-linking. Intensity of irradiation generally is also proportional to the degree of cross-linking. The degree of cross-linking, in turn, generally is proportional to the melting point of the gel and the mechanical strength of the gel, while generally being inversely proportional to the in vivo rate of degradation of the gel.

The rate of crosslinking as well as the byproducts formed by the crosslinking process can be controlled by altering the gaseous environment of irradiation. Specifically, displacement of diatomic oxygen gas in the irradiation chamber, possibly through vacuum or sparging with argon gas, will accelerate the rate of crosslinking and reduce the number of chemical byproducts, e.g., aminochromes.

Following this irradiation, the sheet moves to processing unit 2 (PU2).

PU2 applies auxiliary factors to regulate cellular processes (proliferation, differentiation, localization). Examples of such factors are growth factors, integrin antigens, and cellular debris. In a preferred embodiment, these factors are maintained in solution and are applied in a manner similar to the operation of an inkjet-type printer. Different combinations of factors are applied to the sheet surface in a pattern determined by CU depending on the tissue type. PU2 then crosslinks the applied factors to the GSH sheet substrate. Methods of crosslinking should not neutralize the effects of the factors. Such crosslinking methods include, but are not limited to, application of enzyme, e.g., transglutaminase, UV irradiation, and/or addition of chemical crosslinkers.

To locally modulate GSH sheet stiffness, PU2 applies locally thermal irradiation in a pattern determined by CU. In a preferred embodiment, the thermal radiation source is an infrared laser.

All GSH sheets are then moved into processing unit 3 (PU3) and are stacked or arranged as necessary. Excess crosslinking agents, if any, are be removed via dissolution in PU3.

Still referring to FIGS. 2 and 3, the masked areas of the GSH sheet which have not been converted to a more thermally stable and less soluble material via UV irradiation are removed in PU3. By way of example and not limitation, PU3 may comprise simply a chamber connected to a solvent reservoir and a waste collection unit. The chamber should include a means to hold down flat and secure the GSH sheets, e.g., mechanical clamps or weights or by the generation of electric and/or magnetic fields with supporting materials to produce an electrostatic and/or magnetic force on the sheet. In PU3, the irradiated GSH sheet is first securely clamped to the bottom of the chamber or to a frame located above the bottom. The sheet is then exposed to solvent heated to a temperature equal to or above the melting point of non-irradiated GSH but below the melting point of the irradiated GSH. Exposure to the hot solvent ends when it is determined that enough of the non-irradiated material has dissolved. The sheet is then moved to processing unit 4 (PU4), while the mixture of used hot solvent and dissolved GSH is drawn out of PU3 to the waste collection unit.

In a preferred embodiment, the solvent utilized in PU3 is primarily water. Additives may be added to the water to modulate the dissolution process. By way of example and not limitation, one such additive is acid, which serves to accelerate the dissolution of non-irradiated gelatin. In another embodiment, some additives serve to stabilize the conjugated factors at the elevated temperatures.

Depending on the method used for clamping down the GSH sheet, the design of PU3 will vary. In the case of mechanical clamping, PU3 should include an automated clamp that secures the GSH sheets, such that they do not curl when exposed to hot water. In the case of electronic clamping, PU3 should include a parallel plate unit to generate loci of positive and negative voltage at the top and bottom ends of PU3 (the ends whose area vectors are parallel to those of the GSH sheet). In the case of magnetic clamping, it is advantageous to perfuse or surround the GSH with magnetic material and apply a magnetic field from PU3.

It can also be convenient to temporarily ligate the sheets together and process multiple sheets simultaneously. In one embodiment, this can be done by first applying transglutaminase to the edges of a stack of GSH sheets. This method will help prevent the individual GSH sheets from separating during the dissolution process.

The duration of incubation of the GSH sheet in hot solvent in PU3 should be long enough to remove all unwanted parts of non-irradiated gelatin; longer incubation times will remove more of the non-irradiated gelatin.

According to an alternative embodiment of the invention, a set number of the irradiated GSH sheets are arranged before insertion into PU4 so that a bulk mass can be processed, which can facilitate the transport of structures with large and/or frequent interstitial spaces or other difficult geometries.

Again referring to FIGS. 2 and 3, GSH stacks prepared in PU3 are dried to an appropriate degree in processing unit 4 (PU4) using, for example, streams of dry gas(es). The GSH stacks are then crosslinked. PU4 will then arrange all additional GSH stacks as necessary to create the desired 3D structure.

In one embodiment, the GSH stack is immersed in a solution of reducing sugar(s). The sugar-loaded structure is heated for a sufficient period of time at an appropriate temperature that does not significantly melt the irradiated GSH to fuse the individual sheets together. Once the sheets have been adequately fused, excess sugar solution is removed by washing with water. Waste water from this step is drawn out of PU3 and into the waste collection unit. The material remaining in PU3 is subsequently collected.

The choice of sugar used to prepare the hot sugar solution employed in PU3 will affect the properties of the final product. The sugar should have reasonable reducing strength, as the reaction between protein and sugar resulting from heating (i.e., the Maillard reaction) depends on the sugar having reactive aldehyde or carbonyl groups. Sugars of increasing reducing strength will form cross-links more rapidly and at greater density, which will lead to increased thermal and mechanical durability and a lower rate of degradation. Reasonable increases in sugar solution concentration and/or temperature and/or incubation duration will also lead to increased cross-linked density, which generally will yield greater thermal and mechanical durability and a lower rate of degradation.

Depending on the vertical extent (i.e., height or number of stacked GSH sheets) of the final product, it can be advantageous to fuse the structure in sections: a sequence of GSH sheets less than the total assembly can be fused together through the aforementioned application of sugar solution and heat; these sections will then be fused together by the same process to form the final product. The rationale underlying this alternative approach is that as the number of sheets in the stack increases, the thermal transport properties of the assembly may change and could result in slower rates of polymerization and a lower degree of polymerization with increasing distance from the external surfaces of the assembly.

According to an alternative embodiment, PU4 can instead apply enzymatic crosslinkers. In a preferred embodiment, transglutaminase solution is perfused throughout the arranged GSH stacks received from PU3. The GSH stack(s) are then incubated sufficiently, with the knowledge that increased incubation time will increase crosslink density, leading to greater thermal and mechanical durability and a reduced rate of degradation. As described above, it can be advantageous to fuse the structure in sections, as the mass transfer properties of the assembly may change with increasing size, which could lead to incomplete perfusion of enzyme crosslinker, leading to uneven levels of crosslinking with increasing distance from the external surfaces of the assembly.

The stacked GHS sheets, sometimes referred to herein as GSH stack(s), then enter PU5 which applies additional factors to promote cellular processes. These factors may be unstable at elevated temperatures, hence it is advantageous to add them after processing in hot solvent. PU5 comprises either a fillable chamber and/or a series of robotic injectors. In the case of an object of uniform tissue type, it would be convenient to flood the GSH stack with the appropriate factors. In the case of multiple tissue types, it becomes necessary to perfuse the GSH stack in multiple locations with different factors. In both cases, crosslinkers must be added to conjugate the factors to the GSH stack.

In some embodiments, it is more convenient to move PU4 downstream of PU5.

The apparatus and system of the present invention may be automated such that each of the processing units function automatically and/or each of the processing units function automatically and also function automatically as an interrelated whole.

The advantages of the present invention include, without limitation, the ability to craft complex 3D structures using either simple 2D stencils/masks or directed application of focused radiation, the resulting product's ability to withstand normal human physiological conditions, and inexpensive raw material cost. Additionally, the use of UV radiation and heat for the induction of cross-linking between sugar and gelatin, avoids complications including toxicity that are common with chemical cross-linkers.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Materials and Methods

Gelatin Film Preparation

Gelatin films were prepared using commercial gelatin powder type A (Fisher Scientific CAS#9000-70-8), glucose (dextrose anhydrous; Fisher Scientific, CAS #50-99-7), and distilled deionized water. The films were prepared gravimetrically with a Mettler AB-104S microbalance using 5 cm diameter aluminum weighing pans having a blend ratio of 2:1:2 w/w/w gelatin, glucose, and water (Schuler B (2004) PhD. Dissertation, School of Pharmacy at West Virginia University). The gelatin and glucose powder were homogenized in the pans. Distilled and deionized water was heated to approximately 100° C. and added to the weighed gelatin and glucose. The mixture was quickly blended using a metal spatula until the material was homogenous and viscous. Before solidifying, the mixture was spread thinly across the aluminum pan. Samples having no added sugar were prepared using a 2:1 w/w ratio of gelatin and water.

Ultraviolet Irradiation

Samples were excessively irradiated with 27 J/cm2 in a Spectroline UV cross-linker Model XL-1000 equipped with 254 nm bulbs. After irradiation, films were placed in 50 ml of distilled and deionized water then incubated at 45° C. for 24 hours. Gelatin that was not successfully cross-linked after UV exposure solubilized in the distilled and deionized water. The remaining temperature-stable material was collected by decanting and triple rinsing with distilled water. Samples were then re-suspended in distilled water and stored at 4° C. until analysis. Non-irradiated control samples were hydrated in 50 ml of distilled deionized water and incubated at room temperature for 24 hours prior to refrigeration.

Hygroscopicity

Type A gelatin samples containing glucose were prepared in triplicate and divided into two equal groups. Half of the samples were subjected to the previously described irradiation protocol. All samples were hydrated for 24 hours with the irradiated samples incubated at 45° C. and the non-irradiated samples incubated at room temperature. The samples were then rinsed with distilled and deionized water and allowed to air dry at room temperature on weighing paper for 15 minutes to remove residual water. Approximately 1-1.5 g of the triplicate samples were placed into pre-weighed aluminum pans and dried at 45° C. for 24 hours. The samples were weighed and the percent dry-to-wet mass was calculated.

Calorimetry

A TA Instruments multi-cell differential scanning calorimeter (Model MC DSC) having a detection limit of 0.2 mW was utilized for determination of melting temperature profiles. Instrument calibration was performed using fused silica as a reference standard. Gelatin films were lightly dried on weighing paper to remove excess water and approximately 0.3 g of sample was measured gravimetrically and placed into 1 ml hastelloy ampoules for testing. The MC DSC has four thermal wells, one reference and three sample. Triplicate samples were allowed to equilibrate in the calorimeter for 30 minutes at 10° C. The temperature was then increased linearly at a rate of 0.5° C./min and heat flow recorded having a resolution of 10 seconds from 10° C. to 90° C. The upper limit of 90° C. was utilized to avoid complications with the measurement associated with the water phase change. The samples were then allowed to dry in the open ampoules for 24 hours at 45° C. For accurate heat flow determination, calculations were performed utilizing gravimetrically determined dry samples mass.

Scanning Electron Microscopy

Scanning electron microscopy (SEM) was utilized to detect any visible small-scale surface structural differences in the UV-irradiated and non-irradiated samples. Prior to SEM analysis, water was removed from samples by soaking 0.5 g of wet sample in 10 ml of acetone for 5 minutes; gelatin is nearly insoluble in polar organic solvents such as acetone. The samples were then removed from the acetone and dried in an incubator set at 45° C. Prepared hydrated samples were also freeze dried in a Labconco 2.5 Freezone for 24 hours. Sub-samples of approximately 25 mg were then placed on aluminum support stubs covered with carbon tape and sputter coated with gold/palladium in a Hummer 6.2 sputter coater. Visualization was performed using a Hitachi S-4800 field emission SEM.

Mechanical Testing

An MTS Nanoindenter XP with a Berkovich diamond tip was used to measure the Young's Modulus of the type A gelatin samples (Tiwari A and Hihara L H (2012) Surface and Coatings Tech. 206:4606-4616). A 100 ul sample of 2:8 w/w gelatin, water and a 2:1:8 w/w/w gelatin, glucose, and water sample were liquefied by heating to approximately 100° C. and added to the weighed gelatin and the individual samples were pipetted onto duplicate 1×1 cm2 aluminum stubs before cooling. The higher dilution ratios, compared with those previously used, were necessary to allow for even application of the sample to the aluminum stubs. The aluminum stubs were previously tested using an XP basic hardness, modulus and tip calibration test. The samples were allowed to dry in an incubator at 45° C. for 24 hours. One duplicate of each sample was then irradiated at 27 J/cm2 in the UV cross-linker. The four samples were then mounted on the positioning tray and the hardness and modulus measured using the continuous stiffness measurement option. Fused silica was used as a standard. Six to twelve tests were performed on each sample in different regions to achieve a representative measurement of the nano-mechanical properties.

Raman Microscopy

Raman was performed using a Invictus 785 nm NIR laser and measured with a fiber coupled micro-Raman RXN system (Kaiser Optical Systems Inc., Ann Arbor, Mich.), using a metallic front surface coated plane mirror (Zinin et al. (2007) J. Opt. Soc. Am. B 24:2779). Thin 1 mm samples were prepared on glass slides, and irradiated samples compared with controls. The films were prepared gravimetrically with a Mettler AB-104S microbalance having a blend ratio of 2:1:2 w/w/w gelatin, glucose, and water. The mixture was heated to 100° C. and pipetted onto a glass slide and pressed firmly between another. One slide was removed leaving a material thickness approximately 1 mm thick, determined by microscopy. Samples were irradiated at 27 J/cm2. Measurements were performed in triplicate using individual samples for both non-irradiated and irradiated samples. The resultant Raman spectra were then compared.

UV-Visible Spectrophotometry

UV-Visible spectrophotometry was employed to detect differences in the transmission spectra between UV-irradiated and non-irradiated samples. The sample ratio was modified to a 2:1:16 w/w/w ratio of gelatin, glucose, and water to promote even spreading on fused silica windows. 100 uL of liquefied sample was evenly spread on a 1" fused silica window. The non-irradiated gel-coated window was then dried at 45° C. for two hours. The non-irradiated sample's percent transmittance was then measured in a Perkin Elmer Lambda 2 Spectrophotometer from 190 nm to 1100 nm. The sample was then UV-irradiated with 27 J/cm2 and its percent transmittance measured. The same sample with then placed inverted in a 45° C. water bath for an hour to remove the colored byproduct produced by the glycolytic reaction, dried in the incubator again and re-measured.

Gel Patterning 100 micron-scale patterns were generated on the gels through selective irradiation with UV. Patterns were generated and printed onto gel films with 10% wt ascorbic acid solution using a modified HP Deskjet 1000. The ascorbic acid functioned both as a photomask (Vaid et al. (2005) J. Chem. Soc. Pak. 27:227-232) and as a potential free-radical scavenger (Brand-Williams et al. (1994) LWT-Food Sci. Technol. 28:25-30) to prevent UV-induced cross-linking. The films were then exposed to 27 J/cm2 of UV and were immersed in 90° C. water for 5 minutes. The gels were then recovered and examined with an Olympus BX-43 fluorescence microscope.

Results

Figure 6:
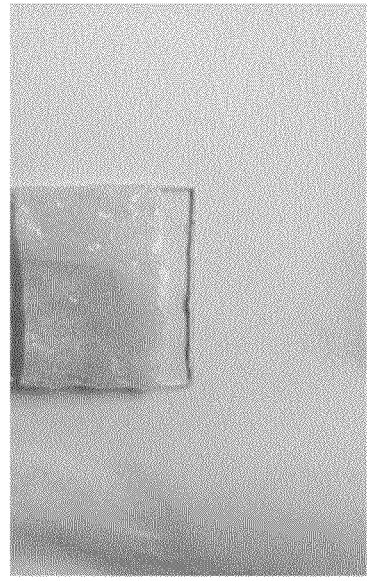
Figure 7:

Irradiation of gelatin-sugar samples results in the formation of a colored hydrogel as seen in the photograph presented in FIGS. 6 and 7. At the irradiation intensities employed in this investigation, this color change was confined to a thin layer at the material's surface. The nominal cross sectional thickness of the films on the slide is about 0.75 mm. Examination of the film cross sections with a light microscope (Olympus BX43) suggests that the color change penetrates less than 20% of the film thickness. Incubation of the irradiated material at 45° C. in an aqueous solution dissolves the uncolored portion, leaving only a thin sheet of hydrated thermostable product. The observed color of the irradiated sample is mostly removed upon incubation in water. This suggests that the compound responsible for the color change is a byproduct of the crosslinking reaction and is not strongly associated with the newly crosslinked molecular arrangement. The exact compound requires further analysis.

An analysis of water absorption capabilities was conducted on crosslinked gelatin obtained after irradiation and incubation at 50° C. relative to non-irradiated samples. On a dry mass basis, the non-irradiated hydrogel is able to retain about 1.6 times as much water when compared to the irradiated samples. Neither sample type had any change of water retention ability between 24 and 48 hours. Based upon the wet mass, the final dry mass percentages remaining after incubation at 50° C. were 5.1+0.6% for the non-irradiated sample compared with 8.4+1.1% for the irradiated sample.

In order to confirm and evaluate quantitatively the apparent thermostability of the UV-irradiated gelatin, samples were tested using differential scanning calorimetry (DSC) and compared to non-irradiated controls. The gelatin polymers were hydrated using the protocol described in the preparation of ultraviolet treated samples prior to analysis with the MC DSC instrument in order to minimize errors associated with differences in water content. The actual dry weights of each sample, which were used to calculate heats of fusion from the DSC data, were determined post-calorimetry as described previously.

Figure 5:
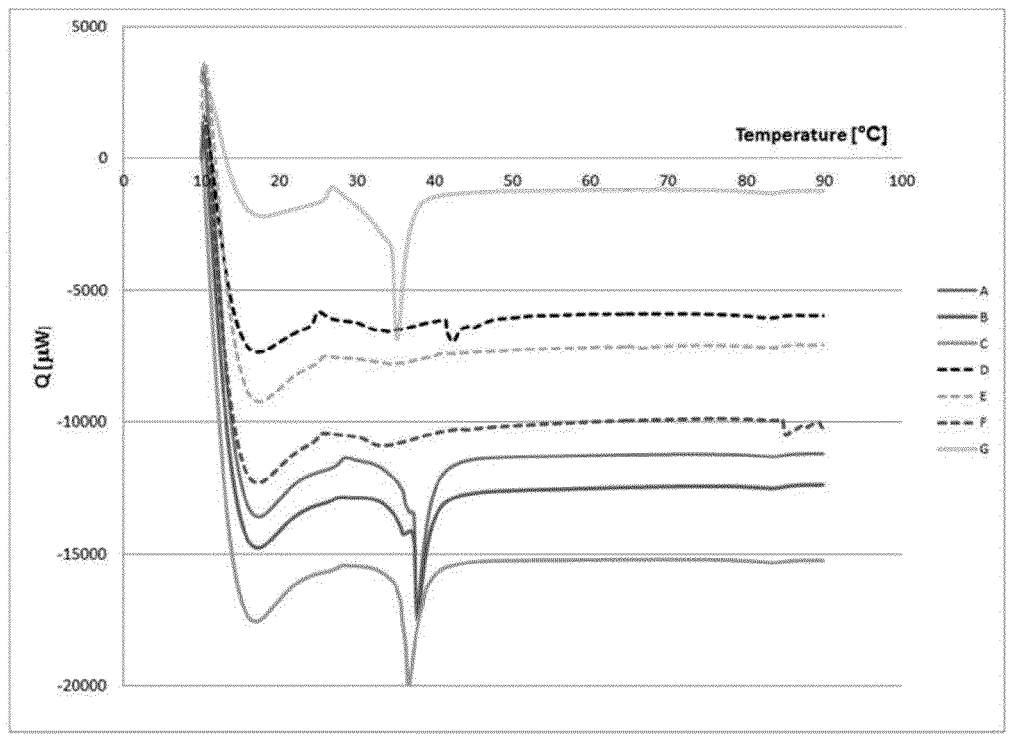

FIG. 5 presents representative thermograms for triplicate replicates of the UV-irradiated gelatin-glucose samples and non-irradiated controls. Additional replicates were analyzed with identical results. For comparison, FIG. 5 also includes a single thermogram for a non-irradiated gelatin sample with no added glucose (FIG. 5G). The seven traces shown in FIG. 5 are reported with slight vertical offsets for image clarity. The initial sharp descent in the curves reflects the transient state that occurs as heating begins following the 30 minute equilibration period at 10° C., during which the sample needed to be constantly cooled. Non-irradiated gelatin-glucose and gelatin (only) samples (FIG. 5; curves A, B, C, and G) all exhibited a sudden, sharp increase in negative (endothermic) heat flow as temperature rose above 34° C. The average melting temperature of the non-irradiated gelatin-glucose controls was determined to be 34.60+0.84° C. from nine replicate measurements. The average heat of fusion values were calculated using sample dry mass and by numeric integration of the chromatogram area. The non-irradiated samples had an average heat of fusion of 45.08+2.35 J/g.

Thermograms of the irradiated samples (FIG. 5; curves D, E, and F), exhibited no changes in heat flow over the measured temperature from 10° C. to 90° C. Visual examination of the ampoule contents after calorimetric measurement confirms these results. The original conformations of the inserted irradiated samples are maintained, unlike non-irradiated controls that have melted and re-solidified in the ampoule well.

Figure 8:
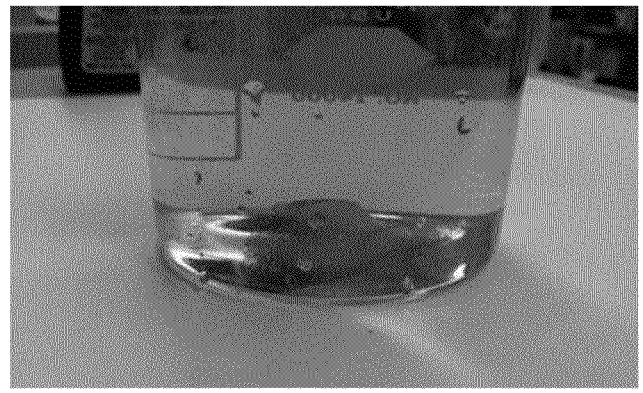
Figure 9:
Figure 10:
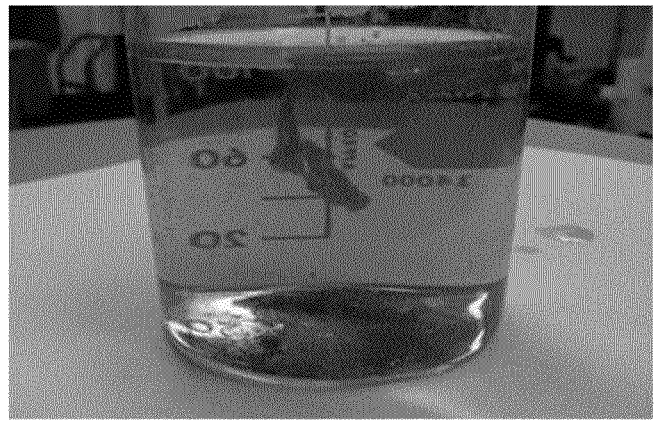
Figure 11:
Figure 12:
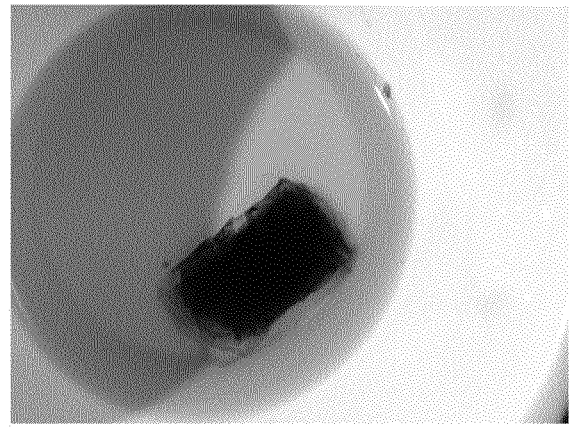
Figure 13:
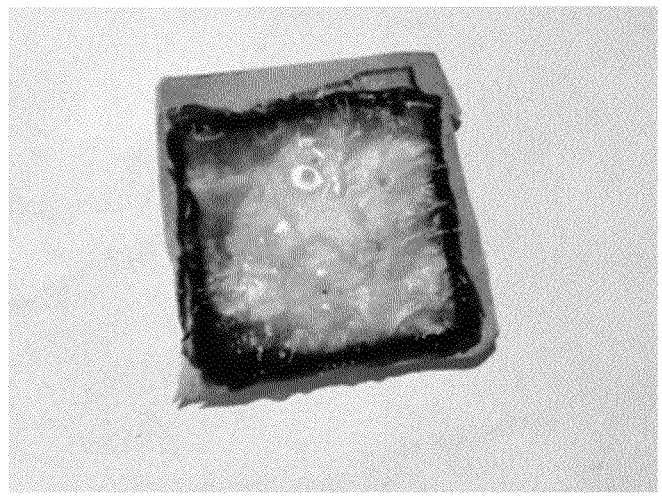
Figure 14:
Figure 15:
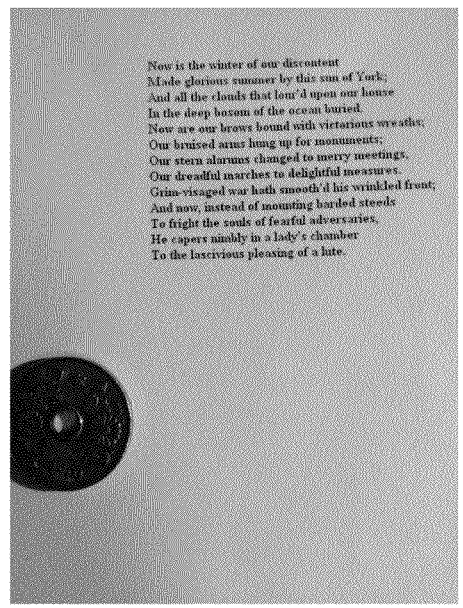
Figure 16:
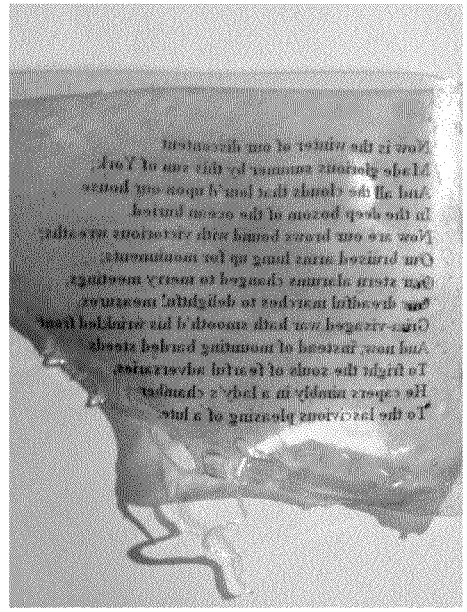
Figure 17:
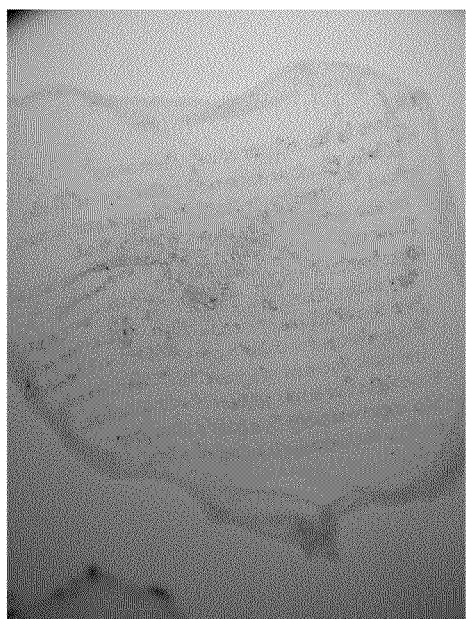
Figure 18:
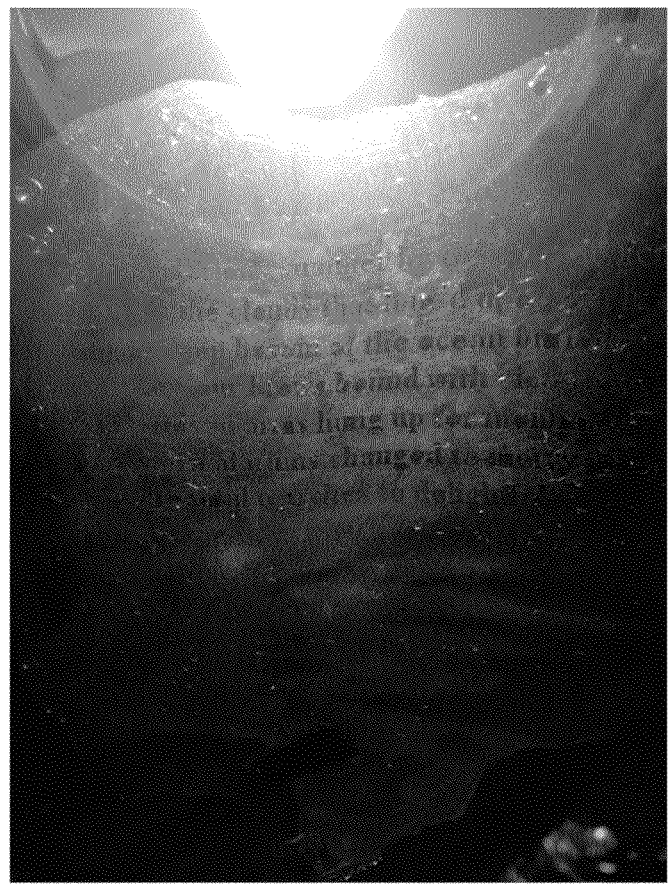

To visually illustrate the structural thermal stability of irradiated gelatin-glucose samples the samples were stained after hydration with a red food coloring dye and placed in an 85° C. water bath for 30 minutes. As seen in FIGS. 8 and 9, the non-irradiated samples were no longer visible, having dissolved completely within 1 minute. The stable physical structure of the irradiated samples are shown in FIGS. 10 and 11, and did not change after 30 minutes of immersion.

Other reducing sugars that include xylose, fructose, and sucrose were substituted in place of glucose. Using this visual method, it was further confirmed that thermal stable polymers were generated upon substitution (Data not shown).

Figure 19:
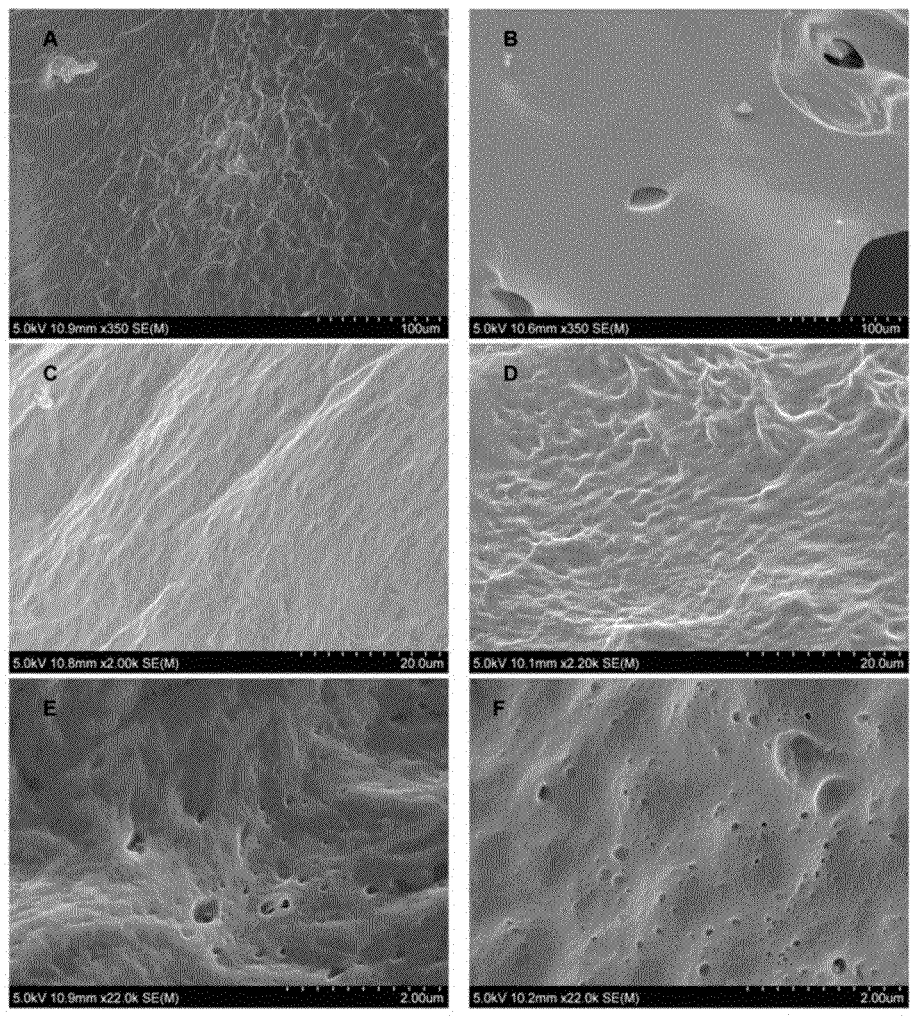

FIG. 19 presents representative results of the field emission SEM analysis conducted to characterize the surface topography and cross section of irradiated and non-irradiated hydrated gelatin-glucose mixtures and to identify any differences in these surface features. Although the photographs suggest that the irradiated sample has a slightly more textured topography than the non-irradiated sample, we were unable to determine if these are artifacts of the sample preparation process. The dehydrated samples were observed to have very small pores under high magnification, but these do not appear to be significant, since they lack any regular distribution. A regular, patterned surface structure was not expected, owing to the amorphous and random ordering of gelatin.

Figure 20:
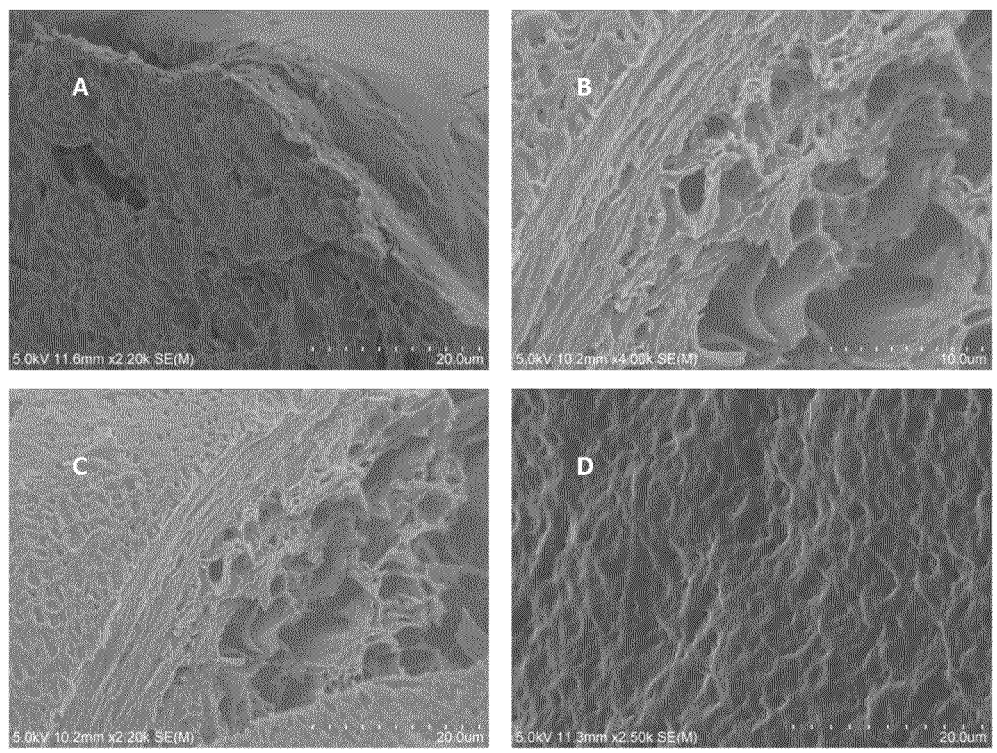

Non-irradiated and irradiated samples were then lyophilized and observed with SEM. The non-irradiated sample's surface is very smooth and non-porous (FIG. 20A) while the irradiated sample's surface appeared to be fibrillar and pockmarked (FIG. 20D). Cross sectional images result in further visual differences. The irradiated sample appears to have a more stratified appearance, where increased density is observed at the surface interface which is directly exposed to ultraviolet irradiation (FIGS. 20B and 20C). The non-irradiated sample appears more homogenous with fewer surface features (FIG. 20A). As previously mentioned, the surface penetration of the UV is limited to micron-scale depths. Crosslinking density may decrease with depth due to UV extinction.

Comparisons of the Raman spectra from the non-irradiated and UV-irradiated gelatin-glucose samples did not show peak differences when the spectra were overlaid (Data not shown).

Figure 21:
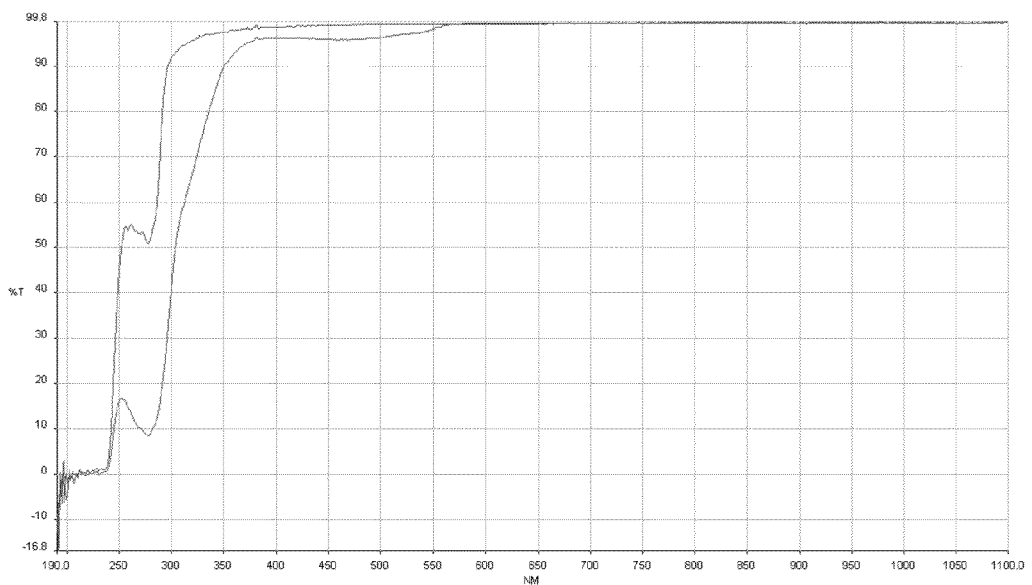

Scanning UV-Visible spectrophotometry was employed to detect absorbance changes in the gelatin composition after crosslinking. FIG. 21 presents the percent transmittance of non-irradiated and UV-irradiated gelatin-glucose gels for wavelengths in the 190-1100 nm range. The peak centered at approximately 280 nm in the non-irradiated sample is potentially attributed to a convolution of absorbance by phenylalanine and tyrosine, which are present in small amounts (Eastoe E (1955) Biochem. J. 61:589-600). Following UV irradiation, the peak centered at approximately 280 nm greatly increases in magnitude and another small peak appears at approximately 475 nm. The reductions in transmittance at 280 nm at 475 nm were thought to be related to the cross-linking mechanism. Because some oxidation products of tyrosine absorb at around 475 nm, e.g. dopachrome and aminochrome (Zafar et al. (2006) Mol. Pharmacol. 70:1079-1086), it was posited that tyrosine oxidation was part of the potential crosslinking pathway. The peaks at 280 and 475 nm are still maintained after soaking irradiated samples in heated water.

FIG. 22 lists the Young's Modulus results from the nanoindentation of the four sample types (+glucose −UV, −glucose −UV, +glucose +UV, −glucose +UV). From these results, the UV-irradiated samples did not show any differences in Young's moduli when compared with non-irradiated controls. However, the inclusion of glucose into the gel changes its mechanical properties. Due to inhomogeneity of the material there is statistical variability within the individual sample measurements. While there are no significant differences in Young's moduli between irradiated and control samples, glucose-containing samples had a 5-6 fold reduction in the Young's Modulus. These trends were repeatable between individual sample preparations.

Lastly, FIG. 23A depicts a sample of selectively UV-irradiated gel at 40× magnification, following immersion in 90° C. water. FIG. 23B depicts the original computer-generated pattern.

Discussion

Prior work has demonstrated that UV radiation-induced cross-linking increases the mechanical strength of collagen and collagen-sugar systems (Ohan et al. (2002) J. Biomed. Mater. Res. A 60:384-391; Tomihata et al. (1994) Polymers of Biological and Biomedical Significance. American Chemical Society. Chapter 24, 275-286; Weadock et al. (1995) J. Biomed. Mater. Res. 29:1373-1379). Gelatin is a denatured form of collagen and has similar chemical properties. Unlike collagen, gelatin is easily solubilized in liquid suspensions and can be cast into complex two- and three-dimensional shapes. Ionic interactions between the gelatin fibrils maintain a degree of structural integrity; however, gelatin rapidly dissolves in excess water and melts at physiological temperatures, which complicates its use as a material for biomimetic scaffolding structures.

Based on the similarities in the chemical structure of gelatin and collagen, and by analogy to the results of Ohan et al. (Ohan et al. (2002) J. Biomed. Mater. Res. A 60:384-391), we posited that the application of UV radiation to a homogeneous gelatin-glucose substrate would promote cross-linking and, consequently, reduce solubility in aqueous media and enhance thermal stability. The results of our experimental investigation support this hypothesis. We were able to create a gelatin polymer that is stable at temperatures of at least 90° C.

There are multiple theories on the mechanism of cross-link formation in collagen. Due to the chemical similarity between collagen and gelatin, we expected that the same mechanisms would apply to gelatin. The first theory proposes that the collagen and sugar molecules undergo the Maillard reaction to form cross-links with neighboring collagen molecules (Ohan et al. (2002) J. Biomed. Mater. Res. A 60:384-391). One of the critical steps in the Maillard reaction is glycation, where the amine group of the protein attacks the reactive carbonyl group of the sugar (Goldin et al. (2006) Circulation 114:597-605). Glycation requires the sugar to be in its linear chain form in order to have access to the reactive carbonyl group; typically, only 0.002% of glucose molecules are in the linear chain form (Ohan et al. (2002) J. Biomed. Mater. Res. A 60:384-391). It has been hypothesized that UV irradiation generates free-radicals which react with the sugar molecules to increase the concentration of linear chain form sugar, which in turn increases the rate of glycation and cross-link formation (Ohan et al. (2002) J. Biomed. Mater. Res. A 60:384-391).

Another mechanism is based on the observation that UV can promote cross-linking in collagen without sugar. Exposure to UV radiation at appropriate wavelengths generates free radicals on aromatic amino acids, e.g., tyrosine and phenylalanine (Weadock et al. (1995) J. Biomed. Mater. Res. 29:1373-1379; Fujimori E (1965) Biopolymers 3:115-119), that can then form intermolecular bonds (Weadock et al. (1995) J. Biomed. Mater. Res. 29:1373-1379; Cooper D R and Davidson R J (1965) Biochem. J. 97:139-147).

We posit that UV irradiation generates free-radicals in solution which accelerate cross-linking between individual gelatin molecules. Addition of antioxidant (L-ascorbic acid) inhibited the crosslinking process (FIG. 7), agreeing with the results of Ohan, et al. Based on our current results, it is difficult to ascertain the mechanism by which the free-radicals react with the gelatin and sugar. Rather than one exclusive pathway for the formation of crosslinks, multiple pathways can potentially exist and proceed in parallel. In the presence of sugar, gelatin undergoes the Maillard reaction and also forms bonds between its radical aromatic residues. Without sugar, gelatin only forms bonds between its radical aromatic residues. The results from the spectrophotometric experiments offer a potential mechanism for crosslink formation between aromatic residues.

The large decrease in transmittance following UV-irradiation at 280 nm in FIG. 6 is thought to be caused by either an increase in tyrosine content or the formation of dityrosyl groups. Typically, tyrosine, cysteine, tryptophan, and, to a much lesser extent, phenylalanine are assumed to be the primary contributors to absorbance at 280 nm (Gill S C and von Hippel P H (1989) Anal. Biochem. 182:319-326). Gelatin lacks tryptophan, but has appreciable quantities of phenylalanine and a lesser amount of tyrosine (Eastoe E (1955) Biochem. J. 61:589-600). It is unlikely for phenylalanine to form under these conditions; however, the conversion of phenylalanine into tyrosine as a result of UV irradiation with low efficiency has been documented (Ishimitsu et al. (1990) Chem. Pharm. Bull. 38:1417-1418). Nevertheless, because the molar extinction coefficient of tyrosine at 280 nm in water is roughly an order of magnitude greater than that of phenylalanine in water, even partial conversion of phenylalanine to tyrosine would significantly reduce transmittance (Lundblad R L and MacDonald F M (2010) Handbook of Biochemistry and Molecular Biology, 4th Edition. Chemical Rubber Company Press, Cleveland, Ohio, pp. 81). Even though the efficiency of phenylalanine conversion noted by Ishimitsu, et al. is relatively low, their experiment used free amino acids whereas the current experimental setup has phenylalanine as part of a protein chain. The intermolecular interaction between gelatin chains and the intramolecular interactions between constituent amino acids may facilitate hydroxyl radical reactions with phenylalanine. Additionally, the absorbance peak that occurs at around 475 nm in the UV-irradiated samples may be indicative of dopachrome or aminochrome content, which are downstream products of tyrosine oxidation and cyclization (Zafar et al. (2006) Mol. Pharmacol. 70:1079-1086; Ishimitsu et al. (1990) Chem. Pharm. Bull. 38:1417-1418).

While the generation of tyrosine from phenylalanine will not result in crosslink formation, two tyrosyl radical groups can react to form a covalently-bound dityrosyl group. Ultraviolet radiation at 254 nm has been shown to generate tyrosine free radicals in aqueous solution (Jin et al. (1995) J. Photochem. Photobiol. A: Chem. 92:147-153). The formation of dityrosyl crosslinks could also contribute to the increased absorbance at 280 nm. The results of Rosei, et al. indicate that dityrosine absorbs more strongly than tyrosine near 300 nm, with a primary peak at around 280 nm (Rosei et al. (1995) Amino Acids 8:385-391). In FIG. 6, the peak at 280 nm also appears to have broadened towards longer wavelengths, which could indicate dityrosyl formation. Experiments involving the UV-irradiation of elastin have also proposed a similar mechanism for crosslinking (Sionkowska et al. (2006) J. Photochem. Photobiol. B: Biol. 85:79-84). Mechanical strength is regarded as an indicator of crosslink density (Ohan et al. (2002) J. Biomed. Mater. Res. A 60:384-391). Our results indicate similar stiffness for both the UV-irradiated and non-irradiated samples, which implies a relatively small concentration of crosslinks. Given that the combined phenylalanine and tyrosine content of gelatin is under 4% wt, with at least twice as much phenylalanine than gelatin, the theoretical number of possible crosslinks is low (Eastoe E (1955) Biochem. J. 61:589-600). Furthermore, the formation of dityrosyl groups is dependent on the presence of free radicals in solution (Jin et al. (1995) J. Photochem. Photobiol. A: Chem. 92:147-153). The introduction of a free radical scavenger ascorbic acid as shown in FIG. 7 strongly inhibits the formation of crosslinks. From these data, the crosslinking mechanism is free-radical dependent and the covalent crosslinks are low in density. Dityrosyl bonds are durable and can withstand extreme conditions of prolonged incubation at 95° C. in 6 N HCl (Felder et al. (2002) Eukaryot. Cell. 1:799-810). Based on the reported durability of dityrosyl crosslinks, such covalent bonds could be responsible for the increased thermal stability of UV-irradiated gelatin.

We were able to achieve reasonably high resolution in our selective irradiation of gel samples (FIGS. 23A and 23B). The smallest feature sizes were about 500 microns in diameter when swollen in water at 36° C. The feature sizes appeared to be limited by the resolution of the printhead, so it is likely that more specialized equipment could produce even finer details. Nevertheless, our smallest achievable pore sizes are comparable to some of the sizes required for tissue growth (Hollister S J (2005) Nat. Mater. 4:518-524). As opposed to conventional methods of pore formation, e.g. electrospinning and freeze-drying, the position of every feature is planned beforehand in this method of selective irradiation. It could be possible to generate gelatin films with the same micron-scale geometry as native tissue scaffolds. Furthermore, the results from the nanoindentation experiments show that the addition of glucose reduces the stiffness of UV-irradiated gels. Modulating gel stiffness could facilitate its processing and handling.

Gelatin has many properties which make it an ideal starting material for cell scaffolds. Native gelatin is easily degraded by proteases, possesses minimal antigenicity (Miskon et al. (2009) J. Artif. Organs 12:111-117; Waksman B H and Mason H L (1949) J. Immunol. 63:427-433), and is very soluble in aqueous solution (Miyahara et al. (1982) J. Gerontol. 37:651-655). Based on our results, cross-linking gelatin renders it insoluble at physiological temperatures; prior work also correlates greater cross-linking density with reduced rate of enzymatic degradation (Tomihata et al. (1994) Polymers of Biological and Biomedical Significance. American Chemical Society. Chapter 24, 275-286). By selectively irradiating sugar-gelatin mixtures with UV, we can generate regions with high resistance to dissolution and thermal degradation. Application of heat and/or protease will then remove the non-irradiated sectors of the gel, allowing the rapid and economical generation of complex gel geometries for use in cell scaffolds.

Conclusion

The current investigation has demonstrated the increased thermal stability and reduced water solubility of gelatin-sugar dispersions cross-linked by UV exposure. By increasing the melting temperature of gelatin, we have removed a major impediment for use of gelatin in tissue engineering applications. Since increased cross-link density generally correlates with increased mechanical strength and resistance to enzymatic degradation, it is also proposed that the described methodology enhances gelatin's ability to serve as a material for cell scaffold applications. The method of cross-link formation is posited to require the generation of free-radicals and the formation of dityrosine between neighboring molecules.

SUMMARY AND SCOPE

In broad embodiment, the present invention is a method, system and apparatus for building complex 3D scaffolds to be used, for example, for in vitro organ growth, to produce internal human or animal organs and/or body parts, using a GSH comprising a mixture of gelatin, sugar, and water, UV radiation, and heat or enzyme.

The advantages of the present invention include, without limitation, the ability to rapidly craft complex 3D structures using relatively cheap feedstock materials and equipment. Additionally, the use of UV irradiation and heat or enzyme for the induction of cross-linking between sugar and gelatin avoids complications including toxicity that are common with chemical cross-linkers. Furthermore, the apparatus and methods described are capable of attaching factors to promote cellular processes on a very fine scale.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but shall be deemed to include all embodiments, methods and equivalents within the scope and spirit of the invention as claimed.

The invention claimed is:

1. A method for building three dimensional biomimetic scaffolds comprising the steps of:
   (a) forming a plurality of irradiated layers, wherein each irradiated layer is created by providing a mixture of gelatin and water, irradiating a portion of the mixture with UV irradiation to form a cross-linked gel layer with at least one non-irradiated region, and dissolving the at least one non-irradiated region to leave an irradiated layer;
(b) stacking a plurality of said irradiated layers; and
(c) fusing said layers together to form a scaffold that exhibits user defined complexity extending in three dimensions.

2. The method of claim 1 wherein the mixture also contains a sugar.

3. The method of claim 2, wherein the relative concentrations of gelatin, sugar and water in the mixture ranges from 2:1:2 (gelatin:sugar:water) w/w/w to 2:1:16 (gelatin:sugar:water) w/w/w.

4. The method of claim 2 wherein the concentration of sugar in the mixture is varied to modulate gel stiffness and ease of processing.

5. The method of claim 2 wherein the mixture is selectively irradiated by tracing a pattern over the mixture using a focused beam radiation source.

6. The method of claim 1 wherein the mixture is selectively irradiated using a diffuse radiation source and a stencil or mask and wherein the stencil or mask is a UV absorbing and/or free-radical neutralizing liquid that is sprayed over the mixture.

7. The method of claim 1 wherein following said irradiation, the non-irradiated material is removed from said gel layer to leave a cross-linked gel layer demonstrating a predetermined irregular shape.

8. The method of claim 7, wherein said removal of said non-irradiated material is accomplished by dissolving said material in a heated solvent.

9. The method of claim 7, wherein said cross-linked gel layer is held in place during the removal step by means of magnetic material exposed to an electromagnetic field.

10. The method of claim 1 comprising the further step of conjugating biochemical factors to said gel layer to stimulate cellular processes.

11. The method of claim 10 wherein the conjugating biochemical factors are selected from a group comprising growth factors, cellular debris, extracellular matrix debris, ligands specific for integrins, viral vectors, acids, bases, transcription factors, DNA, RNA, paracrine factors, endocrine factors, proteins, lipids, and carbohydrates.

12. The method of claim 1 comprising the further step of applying thermal radiation to said gel layer following irradiation to modulate the gel layer's stiffness.

13. The method of claim 1 further comprising the step of fusing a plurality of cross-linked gel layers together to form said scaffold by the application of a fusing means.

14. The method of claim 13, wherein said fusing means is sugar glaze and heat.

15. The method of claim 13, wherein said fusing means is an enzyme.

* * * * *